United States Patent
Earthman et al.

(10) Patent No.: US 11,493,415 B2
(45) Date of Patent: Nov. 8, 2022

(54) SYSTEM AND METHOD FOR DETERMINING STRUCTURAL CHARACTERISTICS OF AN OBJECT

(71) Applicant: Perimetrics, LLC, Newport Beach, CA (US)

(72) Inventors: James C. Earthman, Irvine, CA (US); Cherilyn G. Sheets, Newport Beach, CA (US); John Michael Elam, Woodland Hills, CA (US); Robert Hayman, Los Angeles, CA (US)

(73) Assignee: Perimetrics, Inc., Redmond, WA (US)

( * ) Notice: Subject to any disclaimer, the term of this patent is extended or adjusted under 35 U.S.C. 154(b) by 719 days.

(21) Appl. No.: 16/475,101

(22) PCT Filed: Dec. 30, 2017

(86) PCT No.: PCT/US2017/069164
§ 371 (c)(1),
(2) Date: Jun. 30, 2019

(87) PCT Pub. No.: WO2018/126244
PCT Pub. Date: Jul. 5, 2018

(65) Prior Publication Data
US 2019/0331573 A1    Oct. 31, 2019

Related U.S. Application Data

(60) Provisional application No. 62/441,085, filed on Dec. 30, 2016.

(51) Int. Cl.
*G01N 3/30* (2006.01)
*A61B 5/00* (2006.01)
(Continued)

(52) U.S. Cl.
CPC .............. *G01N 3/30* (2013.01); *A61B 5/4547* (2013.01); *A61C 17/224* (2013.01); *A61C 19/04* (2013.01);
(Continued)

(58) Field of Classification Search
CPC .............. G01N 3/30; G01N 2203/0676; A61B 5/0051; A61B 5/4547; A61B 9/00;
(Continued)

(56) References Cited

U.S. PATENT DOCUMENTS 2,428,689 A * 10/1947 Sykes .................... A61C 19/04
433/157
3,176,505 A * 4/1965 Hendrickson ............ G01H 1/00
73/579

(Continued)

FOREIGN PATENT DOCUMENTS

GB        2136569 A       9/1984
JP        09-093067 A     4/1997
(Continued)

OTHER PUBLICATIONS

Barzin, et al., Mechanical Biocompatibility of Dental Implant Materials, Proceedings of the Fourth Pacific Rim International Conference on Materials, Japanese Institute of Metals, pp. 2492-2953 (2002) (4 sheets).

(Continued)

*Primary Examiner* — Nathaniel T Woodward
*Assistant Examiner* — Philip L Cotey
(74) *Attorney, Agent, or Firm* — Quan & Associates; Christopher Quan; Nancy Quan

(57) ABSTRACT

The present invention relates generally to a system and method for measuring the structural characteristics of an object. The object is subjected to an energy application processes and provides an objective, quantitative measure-
(Continued)

ment of structural characteristics of an object. The system may include a device, for example, a percussion instrument, capable of being reproducibly placed against the object undergoing such measurement for reproducible positioning. The system does not include an external on/off switch or any remote on/off switching mechanism. The system also includes a disposable feature or assembly for minimizing cross-contamination between tests. The structural characteristics as defined herein may include vibration damping capacities, acoustic damping capacities, structural integrity or structural stability.

21 Claims, 10 Drawing Sheets

(51) Int. Cl.
   A61C 17/22       (2006.01)
   A61C 19/04       (2006.01)
   G06F 1/3203      (2019.01)
   A61B 9/00        (2006.01)
   A61B 5/11        (2006.01)
(52) U.S. Cl.
   CPC .......... *G06F 1/3203* (2013.01); *A61B 5/0051* (2013.01); *A61B 5/1111* (2013.01); *A61B 9/00* (2013.01); *A61B 2560/0418* (2013.01); *A61B 2560/0425* (2013.01); *G01N 2203/0676* (2013.01)
(58) Field of Classification Search
   CPC .......... A61B 5/1111; A61B 2560/0418; A61B 2560/0425; A61C 17/224; A61C 19/04; G06F 1/3203
   See application file for complete search history.

(56)                References Cited

U.S. PATENT DOCUMENTS

| | | | | |
|---|---|---|---|---|
| 3,833,115 A * | 9/1974 | Schapker | G01K 13/25 | 600/549 |
| 4,157,709 A * | 6/1979 | Schuster | A61B 10/0291 | 600/572 |
| 4,231,259 A * | 11/1980 | Thiruvengadam | G01N 29/11 | 73/584 |
| 4,314,519 A * | 2/1982 | Yunoki | B63B 11/04 | 114/184 |
| 4,341,519 A * | 7/1982 | Kuhn | A61C 1/07 | 433/121 |
| 4,470,810 A * | 9/1984 | Bourdeau | A61C 19/04 | 33/514 |
| 4,482,324 A * | 11/1984 | Wohlgemuth | G01N 3/317 | 433/29 |
| 4,499,906 A * | 2/1985 | Wohlgemuth | G01N 3/317 | 600/589 |
| 4,519,245 A * | 5/1985 | Evans | G01N 29/045 | 73/579 |
| 4,689,011 A * | 8/1987 | Wohlgemuth | A61C 19/04 | 433/121 |
| 4,764,114 A * | 8/1988 | Jeffcoat | A61C 19/043 | 33/514 |
| 4,963,095 A * | 10/1990 | Weissman | A61C 5/90 | 433/118 |
| 4,979,898 A * | 12/1990 | Rand | A61B 9/00 | 33/513 |
| 4,995,403 A * | 2/1991 | Beckman | A61C 19/043 | 433/118 |
| 5,066,142 A * | 11/1991 | DeFrank | G01J 5/021 | 374/E1.013 |
| 5,119,803 A * | 6/1992 | Fishman | A61C 19/063 | 433/80 |
| 5,143,069 A * | 9/1992 | Kwon | G01N 29/348 | 600/442 |
| 5,144,753 A * | 9/1992 | Murphy | G01B 5/18 | 33/514 |
| 5,318,442 A * | 6/1994 | Jeffcoat | A61C 19/043 | 600/589 |
| 5,318,445 A * | 6/1994 | Meier | A61C 17/20 | 433/121 |
| 5,392,779 A * | 2/1995 | Meredith | A61B 5/4547 | 600/437 |
| 5,402,781 A * | 4/1995 | Dimarogonas | A61B 9/00 | 600/407 |
| 5,454,718 A * | 10/1995 | Strohmaier | A61B 17/162 | 433/122 |
| 5,476,009 A * | 12/1995 | Dimarogonas | G01N 29/11 | 73/811 |
| 5,518,008 A * | 5/1996 | Cucchiaro | A61B 9/00 | 600/590 |
| 5,587,284 A * | 12/1996 | Brattesani | A61C 19/043 | 433/29 |
| 5,614,674 A * | 3/1997 | Dimarogonas | G01N 29/11 | 73/584 |
| 5,652,386 A * | 7/1997 | Dimarogonas | G01H 1/16 | 702/56 |
| 5,755,571 A * | 5/1998 | Companion | A61C 19/043 | 33/514 |
| 5,836,891 A * | 11/1998 | Dimarogonas | A61B 5/4504 | 600/587 |
| 5,882,194 A * | 3/1999 | Davis | A61C 1/088 | 433/91 |
| 5,882,197 A * | 3/1999 | Davis | A61C 17/08 | 433/91 |
| 5,951,292 A * | 9/1999 | Lee | G01H 1/12 | 600/589 |
| 6,024,711 A * | 2/2000 | Lentle | A61B 8/0875 | 600/587 |
| 6,120,466 A * | 9/2000 | Earthman | A61B 9/00 | 600/553 |
| 6,149,429 A * | 11/2000 | Bukowski | A61C 17/0202 | 433/80 |
| 6,213,958 B1 * | 4/2001 | Winder | A61B 8/42 | 600/442 |
| 6,234,975 B1 * | 5/2001 | McLeod | A61B 5/0051 | 600/587 |
| 6,242,063 B1 * | 6/2001 | Ferrera | A61L 29/049 | 525/166 |
| 6,274,242 B1 * | 8/2001 | Onodera | B32B 15/08 | 428/480 |
| 6,328,695 B1 * | 12/2001 | Vammen | A61B 8/0875 | 600/442 |
| 6,468,215 B1 * | 10/2002 | Sarvazyan | A61B 8/0875 | 600/449 |
| 6,643,552 B2 * | 11/2003 | Edell | A61N 1/05 | 607/148 |
| 6,730,377 B2 * | 5/2004 | Wang | A61L 29/04 | 604/509 |
| 6,797,198 B1 * | 9/2004 | Miyashita | C09K 19/52 | 252/299.01 |
| 6,818,763 B2 * | 11/2004 | Vukovich | C07F 7/003 | 540/121 |
| 6,918,763 B2 * | 7/2005 | Huang | A61B 5/1111 | 33/513 |
| 6,997,887 B2 * | 2/2006 | Earthman | A61B 8/0875 | 600/553 |
| 6,998,616 B2 * | 2/2006 | Favro | G01N 29/348 | 250/341.6 |
| 7,001,551 B2 * | 2/2006 | Meredith | A61L 27/365 | 264/109 |
| 7,008,385 B2 * | 3/2006 | Earthman | A61C 19/04 | 600/553 |
| 7,022,076 B1 * | 4/2006 | Kantorovich | A61B 8/0875 | 600/449 |
| 7,078,075 B1 * | 7/2006 | Werenicz | B32B 7/12 | 156/244.11 |
| 7,147,467 B2 * | 12/2006 | Shoji | A61C 19/04 | 433/72 |

(56) References Cited

U.S. PATENT DOCUMENTS

| | | | | | |
|---|---|---|---|---|---|
| 7,217,128 | B2* | 5/2007 | Atkin | ............... | A61C 17/20 433/119 |
| 7,607,972 | B2* | 10/2009 | Groman | ............... | A61C 3/025 451/90 |
| 7,766,656 | B1* | 8/2010 | Feine | ............... | A61C 5/62 433/89 |
| 8,241,094 | B2* | 8/2012 | Groman | ............... | B29D 23/00 451/38 |
| 8,435,034 | B2* | 5/2013 | Gersh | ............... | A61C 17/20 433/119 |
| 8,529,313 | B2* | 9/2013 | Groman | ............... | A61C 3/025 451/38 |
| 8,535,300 | B2* | 9/2013 | Boitor | ............... | A61B 18/22 606/16 |
| 8,540,700 | B2* | 9/2013 | Di Sessa | ............... | A61B 18/22 606/1 |
| 2002/0143268 | A1* | 10/2002 | Meredith | ............... | A61B 5/1111 600/552 |
| 2002/0177790 | A1* | 11/2002 | Meredith | ............... | A61C 8/00 600/587 |
| 2003/0191417 | A1* | 10/2003 | Welt | ............... | A61H 13/00 601/134 |
| 2004/0116823 | A1* | 6/2004 | Earthman | ............... | A61B 8/0875 73/12.01 |
| 2005/0003323 | A1* | 1/2005 | Katsuda | ............... | A61B 1/0676 433/29 |
| 2005/0113691 | A1* | 5/2005 | Liebschner | ............... | A61B 5/4504 600/437 |
| 2006/0161074 | A1* | 7/2006 | Liao | ............... | G01K 13/20 374/E1.004 |
| 2007/0179353 | A1* | 8/2007 | Fraden | ............... | A61B 5/6843 600/300 |
| 2009/0056427 | A1* | 3/2009 | Hansma | ............... | A61B 5/441 600/562 |
| 2010/0168615 | A1* | 7/2010 | Amano | ............... | A61B 5/1519 600/583 |
| 2010/0240962 | A1* | 9/2010 | Contant | ............... | A61B 5/1125 600/300 |
| 2011/0259076 | A1* | 10/2011 | Faulkner | ............... | A61B 9/00 73/1.01 |
| 2011/0311944 | A1* | 12/2011 | Earthman | ............... | A61C 8/0089 433/119 |
| 2012/0110763 | A1* | 5/2012 | Jungnickel | ............... | A46B 15/0044 15/105 |
| 2013/0122466 | A1* | 5/2013 | Connor | ............... | G01N 3/42 600/553 |
| 2013/0174639 | A1* | 7/2013 | Earthman | ............... | A61B 5/1111 367/189 |
| 2014/0227652 | A1* | 8/2014 | Park | ............... | A61C 19/04 433/2 |
| 2015/0348320 | A1* | 12/2015 | Pesach | ............... | G06T 7/70 382/128 |
| 2016/0178496 | A1* | 6/2016 | MacDougall | ............... | G01L 5/0052 73/12.01 |
| 2020/0337630 | A1* | 10/2020 | Earthman | ............... | A61B 5/0534 |

FOREIGN PATENT DOCUMENTS

| | | |
|---|---|---|
| WO | 1991016862 A2 | 11/1991 |
| WO | 2008092125 A | 7/2008 |
| WO | 2011160102 A3 | 4/2012 |

OTHER PUBLICATIONS

Koprinarov, Ivaylo, Extended European Search Report for EP 11188989.5, European Patent Office (dated Mar. 19, 2012) (14 sheets).

* cited by examiner

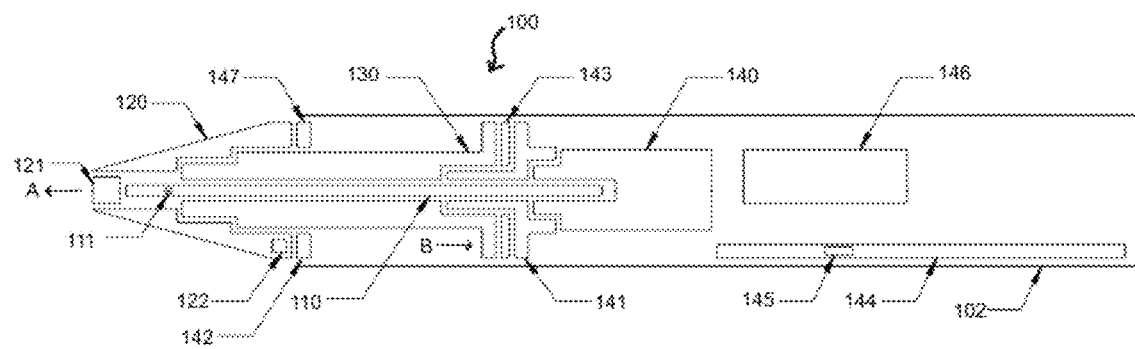
*Fig.1.*
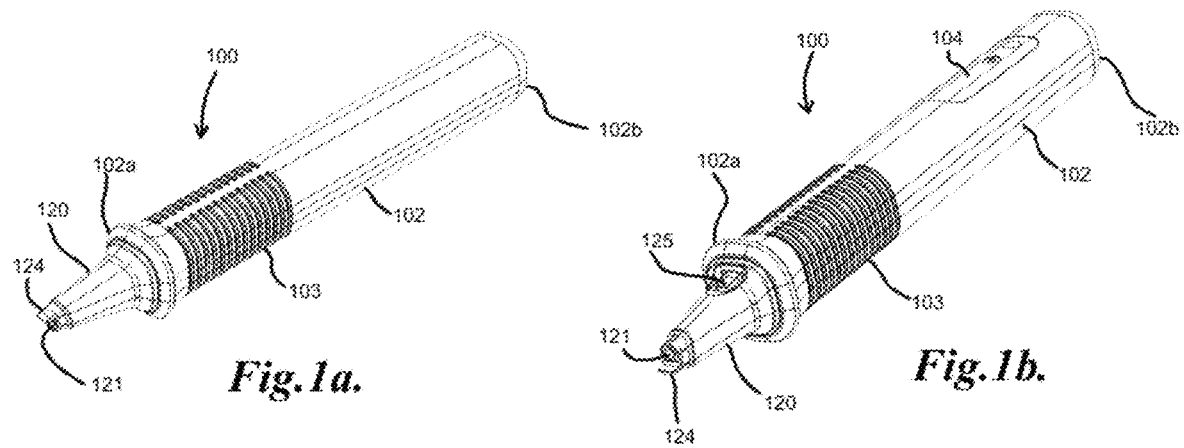
*Fig.1a.*   *Fig.1b.*
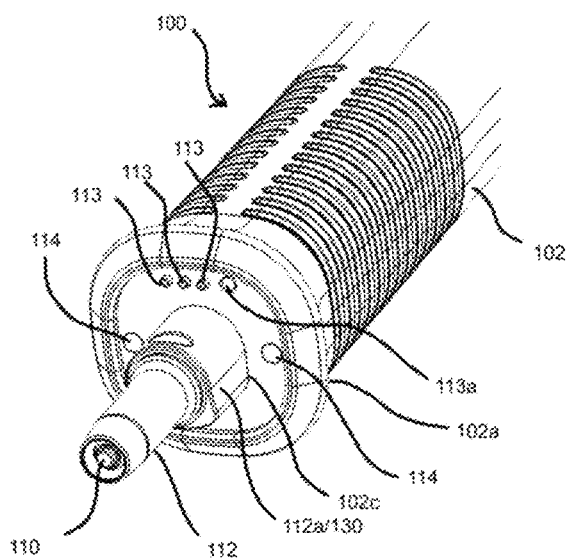
*Fig.1c.*
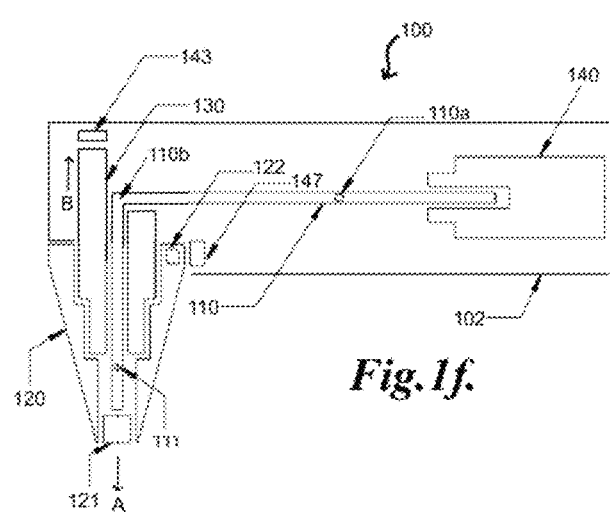
*Fig.1f.*

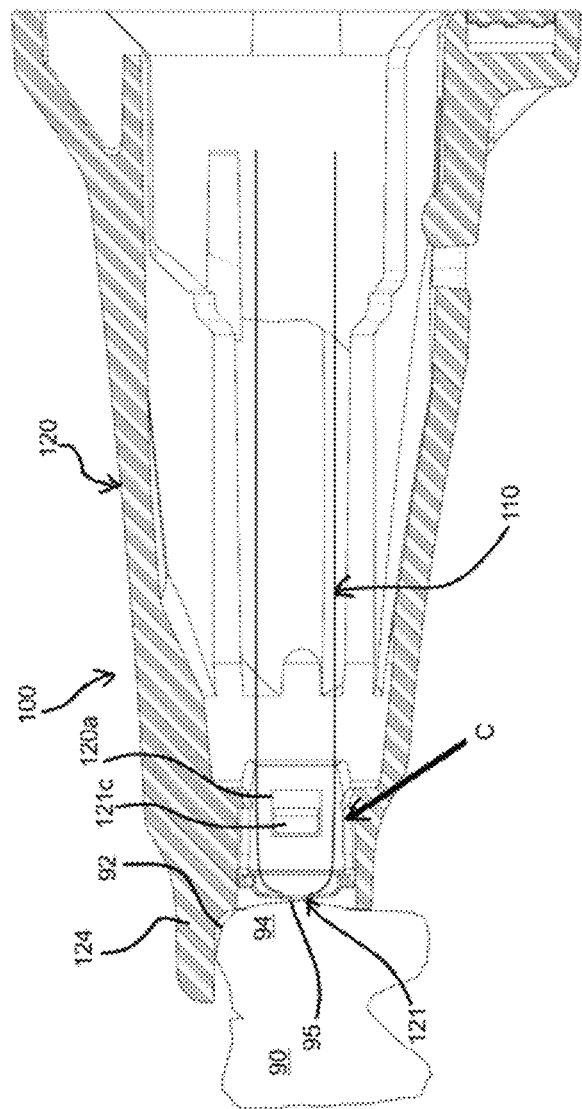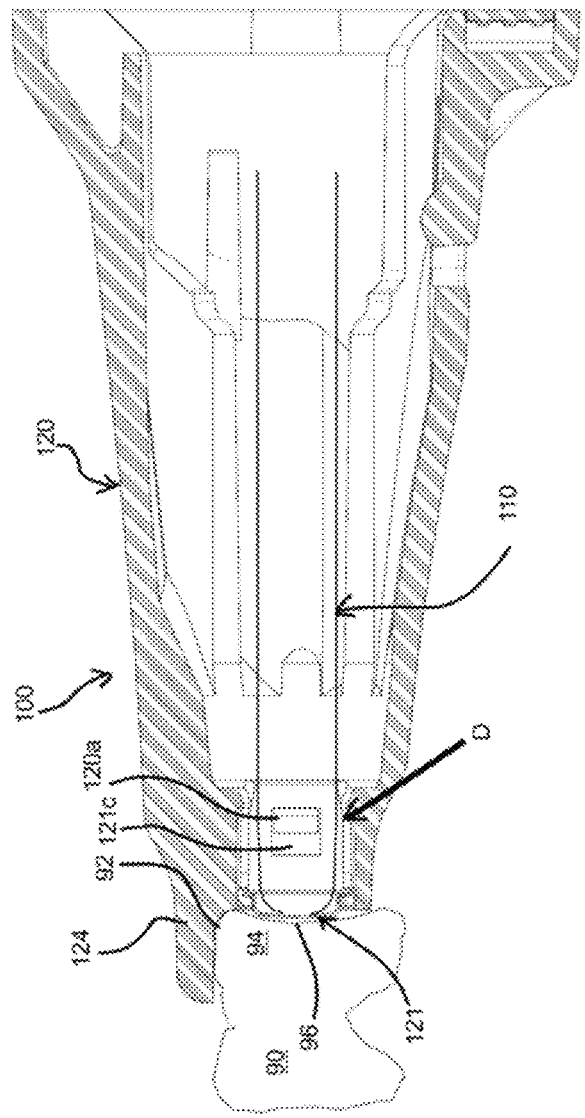

SYSTEM AND METHOD FOR DETERMINING STRUCTURAL CHARACTERISTICS OF AN OBJECT

CROSS-REFERENCE TO RELATED APPLICATIONS

This application is a 371 U.S. national stage application of Patent Cooperation Treaty international application Ser. No. PCT/US17/69164, filed Dec. 30, 2017, entitled "SYSTEM AND METHOD FOR DETERMINING STRUCTURAL CHARACTERISTICS OF AN OBJECT", which claims the priority and benefit of U.S. provisional patent application Ser. No. 62/441,085, filed Dec. 30, 2016, entitled "SYSTEM AND METHOD FOR DETERMINING STRUCTURAL CHARACTERISTICS OF AN OBJECT", the contents of all of which are hereby incorporated by reference in their entireties.

FIELD OF THE INVENTION

This invention relates generally to evaluation of the structural properties of an object; and more specifically relates to evaluation of the structural characteristics that reflects the integrity of an object; after subjecting to an energy application thereon.

BACKGROUND OF THE INVENTION

When an object is subjected to an impact force, a stress wave is transmitted through the object. This stress wave causes deformations in the internal structure of the object. As the object deforms it acts, in part, as a shock absorber, dissipating a portion of the mechanical energy associated with the impact. The ability of the object to dissipate mechanical energy, commonly referred to as the "damping capacity" of the object, depends on several factors, including the type and structural integrity of the materials making up the object.

There are instruments that are capable of measuring the damping capacity of an object. An example of such an instrument is described in U.S. Pat. No. 6,120,466 ("the '466 patent"). The instrument disclosed in the '466 patent provides an objective, quantitative measurement of the damping capacity of an object, referred to as the loss coefficient 17. The energy of an elastic wave attenuates relatively quickly in materials with a relatively high loss coefficient, whereas the energy of an elastic wave attenuates relatively slowly in materials with a relatively low loss coefficient.

The damping capacity of an object is an important parameter in a wide variety of applications. For example, in the field of dentistry, when a healthy tooth is subjected to an impact force, the mechanical energy associated with the impact is primarily dissipated by the periodontal ligament. Changes in the structure of the periodontal ligament that reduce its ability to dissipate the mechanical energy associated with an impact force, and thus reduce overall tooth stability, can be detected by measuring the loss coefficient of the tooth.

SUMMARY OF THE INVENTION

The present invention relates to a system and method for measuring structural characteristics of an object. The object may be subjected to an energy application process and the system is adapted for providing an objective, quantitative measurement of structural characteristics of the object after the energy application process. The system and method is capable of generating more reproducible measurements and better able to detect any abnormalities that may be present in an object.

The system provides a non-destructive method of measurement and may include an instrument, for example, a percussion instrument, having at least a portion capable of being reproducibly placed in contact with the object undergoing such measurement for more reproducible measurements. The system may be turn on and off without an external switch, or remote control. Generally, any external switching device such as a flip switch, a rocking switch or a push button switch, may tend to restrict the manner an operator holds the instrument and thus may restrict the positioning of the instrument on the object, if it is handheld, for example, during measurement so as to enable easy access by the operator to the switching device for turning it on and/or off. To gain flexibility in positioning the instrument, voice control or remote control may generally be used, though such voice controls or remote controls can add complexity to the system. In the present invention, the same advantages of flexibility may be gained without such remote controls or added complexities.

In one exemplary embodiment, the system may include an instrument having a housing with a hollow interior with an open end and an energy application tool, for example, a tapping rod, or impact rod mounted inside the housing for movement inside the housing. Located at the open end of the housing may be a sleeve-portion.

The sleeve portion may be open at its free end, with an object resting, pressing or contacting portion for resting on, pressing or contacting at least a portion of an object during measurement. The contact by the sleeve portion aids to stabilize the device on the object. During measurement, the force exerted by the sleeve portion on an object is controlled by an operator, and a proper force on the object may be important and may need to be monitored, since, for example, either insufficient or excessive force exerted by an operator may complicate the measurements, and may even produce less accurate results. A sensor disposed inside the housing, not physically or mechanically coupled to the energy application tool may be present to ensure that a proper contact force by the contacting portion of the sleeve portion may be applied by the operator for better reproducibility, even by different operators.

The drive mechanism may be an electromagnetic mechanism, and may include an electromagnetic coil and a permanent magnet secured to the back end of the energy application tool, for example, the tapping rod by an interface, for example, a coil mount. The electromagnetic coil may lie axially behind the permanent magnet, for example. The electromagnetic coil may also act directly on a metallic or conductive component, such as a ferromagnetic component. Other forms of linear motors may also be employed.

The sleeve portion may be mounted onto a force transfer sleeve like component, or force transfer member, that forms a permanent part of the front of the housing or protrudes from it, and shields the energy application tool, for example, the tapping rod from damage when no sleeve portion is present, for example, the sleeve portion may form part of a disposable assembly, as discussed below. The force transfer sleeve like component sits around the energy application tool, or rod, and is held at the front by the housing and mounts onto the front of the electromagnetic coil at the rear. The force transfer sleeve like component may be adapted to slide a small amount, and in doing so, may act on a force sensor, for example, a force sensitive resistor, located between the back surface of the force transfer sleeve like component and the coil mount. The energy application tool, for example the tapping rod may be triggered when the object contacting portion of the sleeve portion is pushed against an object undergoing measurement, for example, a tooth and a force may be detected. When a correct force within a certain range is detected, the instrument is turned on to start the measurement.

The sensor, for example the force sensor, may be in physical proximity and/or contact and/or coupled with at least a portion of the device other than the energy application tool, for example, it may be in physical proximity and/or contact and/or coupled with the housing and/or sleeve portion, if the open end of the sleeve portion includes an object contacting portion, as noted above. In one embodiment of the invention, the sensor may include at least one strain gauge for sensing. The strain gauges may be attached or mounted to a cantilever between the device housing and the sleeve portion so that when the object contacting portion of the sleeve portion is pressed on the object it also deforms the cantilever which is measured by the strain gauge, thus providing a force measurement. In some embodiments, multiple strain gauges mounted to a single or to separate cantilevers may be utilized. The cantilever(s) may also, for example, be present on a separate component from the rest of the housing or sleeve portion, such as, for example, on a mounting device. In another embodiment of the invention, the sensor may include a sensing pad which may be positioned between a rigid surface and a sliding part so that when the pad is pressed or squeezed as the sliding part moves towards the rigid surface, the force is measured. According to one embodiment, the rigid surface may be, for example, a coil interface that holds the electromagnetic coil in the drive mechanism within the device housing. The sliding part may be a force transfer sleeve like component disposed inside the housing and coupled to the object contacting portion of the sleeve portion and adapted to slide inside the housing when a force is exerted by the object contacting portion of the sleeve portion on an object. In some embodiments, it may be disposed inside the sleeve portion. The sliding distance may be very small, for example, in the order of about (in millimeters or mm) 0.3 mm to about 1 mm, more for example about 0.5 mm. The sensing pad may include a layer structure, which may be generally referred to as a "Shunt Mode FSR (force sensing resistor) that may change resistance depending on the force applied to the pad, to provide a force measurement. According to another embodiment, the force transfer sleeve like component may be biased forward by a spring, so that when force is applied by the object contacting portion of the sleeve portion on the object, the force transfer sleeve like portion may transfer the force against the spring. According to one aspect, the force sensing may be done by a linear position sensor, which would know, for example, that if the force transfer sleeve like portion is at position X, a force of Y has to be applied to it (against the reaction force of the spring) to move it to that position. According to another aspect, the force sensing may be performed by an optical sensor, for optically sensing the position of the moving part, when it is pushed against a spring. In yet another embodiment of the invention, the relative position of the object contacting portion of the sleeve portion on the object may be determined by having one or more strain gauges which may be attached at one end to a moving part, for example, the force sensor sleeve like component, and the other end to a static element, for example, the housing. In a further embodiment of the invention, the device may include piezoelectric elements for directly measuring the force. In yet a further embodiment of the invention, a hall effect sensor may be used to detect a change in the magnetic field when a magnet (attached to the moving element) is moving relative to the position of the sensor. In yet another embodiment of the invention, a capacitive linear encoder system, like that found in digital calipers may be used to measure the force.

Though the sensor is not physically or mechanically coupled to the energy application tool, it may be in electronic communication with the energy application tool and may act as an on/off switch for the device or instrument, as noted above. For example, when a proper force is exerted on the object by the object contacting portion of the sleeve, it may trigger the activation mechanism of the device or instrument to activate the movement of the energy application tool to start a measurement. Thus, no external switches or push buttons are needed to activate the on and off of the system, as noted above. The indication of the proper force may be indicated by visible or audible signals.

In one embodiment, the instrument may be instantaneously turned on once a proper contact force is exerted by the object contacting portion of the sleeve on the object, as indicated by visible or audible signals. In another embodiment, there may be a delay prior to turning on the instrument once a proper contact force is exerted by the object contacting portion of the sleeve on the object, as indicated by visible or audible signals. In a further embodiment, once a certain push force between the object contacting portion of the sleeve portion and the object is detected and maintained for a period of time, for example, about 1 second, more for example, about 0.5 seconds, the instrument may be turned on to start measurement. In this embodiment, a green light lights up the tip, and percussion will begin approximately 1 second, more for example, 0.5 sec after a force in the correct range is maintained.

The proper force exerted by the operator on the object, for example, through the sleeve portion, acts as a switch of the system. When the system is not switched on, it may be desirable to know whether it has malfunction, not sufficient force or too much force is exerted. In one embodiment, the force measurement may be connected to a visual output, such as lights. Lights may be mounted at any convenient location on the device or instrument, for example, one or multiple LEDs may be mounted at the front of the device or instrument. In one aspect, a multiple light system may be included. For example, two LEDs may be used. When the force is in the correct range, the green light may be lit. If too much force is detected, the LEDs may change to red, and the instrument will not work unless the push force is reduced. In some embodiments, if the user is pushing too hard on the object, the light may change first to amber, then to red. If the push force is sufficient to change the light to red, percussion may either not be started, or be interrupted if it has already started. In addition, there may be an amber LED state which warns when the user is approaching too much push force. At that stage, the instrument may still operate when the LEDs are lit amber. In another aspect, no light may indicate too little force, a green light may indicate the right amount of force, while a red light may indicate too much force. In yet another aspect, a one light system may be included. For example, no light may give a signal of too little force and a red light may give a signal of too much force. In a further aspect, a flashing red light may indicate too much force and no light may indicate too little force.

In another embodiment, the force measurement may be connected to an audible output. In one aspect, the audible output may include a beeping sound to indicate too little force and a multiple beep to indicate too much force. In another aspect, the audible output may include a beeping sound to indicate too little force and a beeping sound with a flashing red light to indicate too much force. In a further aspect, the force measurement may be connected to a voice alert system for alerting too much force or too little force. In yet a further aspect, the force measurement may be connected to a voice alert system to alert too little force and a voice alert and a flashing red light for alerting too much force.

When the force sensor acts as an on/off switch, it may also act to monitor that a proper force is exerted by the object contacting portion of the sleeve portion during measurement and/or a proper alignment of the object contacting portion of the sleeve portion against the object during measurement is obtained. An inclinometer may be present, for example, as part of an electronic control system, which may trigger an audible warning when the device is outside of the angular range of operation, for example, for a tapping rod, it may trigger the warning when it is plus/minus approximately 45 degrees, more for example, 30 degrees from horizontal. If the device is oriented such that the axis of operation is greater than about 45 degrees, more for example, greater than about 30 degrees from horizontal when a push force is sensed on the object contacting portion of the sleeve portion, it may result in a warning sound being emitted by a speaker located on the device, such as the printed circuit board (PCB) within the device. In such circumstances, the percussion action will not begin until the device is returned to an acceptable angle. In some instances, if the percussion action has started when the above-mentioned departure from the range is detected, the device may not actually stop operation, but may simply be sounding an alarm, so that corrections may be made.

The energy application tool has a length with a resting configuration and an active configuration. The movement may be axial movement along the longitudinal axis of the housing, or for oscillatory movement about the longitudinal axis of the housing.

In one embodiment, the resting configuration may be a retracted form and the active configuration may be an extended form when the energy application tool moves axially along the longitudinal axis of the housing, and the retracted form being retracted from the extended form. The movement of the energy application tool, for example, a tapping rod, may be effected by a drive mechanism mounted inside the housing for driving it axially within the housing between a retracted position and an extended position during operation. In the extended configuration, the free end of the energy tool may extend or protrude from the open end of the housing or sleeve portion, if one is present, and substantially extended to contact the object undergoing measurement. The instrument may be of any size including a size that enables measurements be undertaken at locations which are relatively inaccessible such as, for example, in the molar area of a patient's teeth.

In another embodiment, the resting configuration of the energy application tool may be a form that is substantially parallel to the longitudinal axis of the housing, and the active configuration may be in a form making an acute angle with the longitudinal axis of the housing. Thus, during operation, the energy application tool oscillates from the substantially parallel position to the longitudinal axis of the housing to a position making an acute angle with the longitudinal axis of the housing about the pivot point. The energy application tool may be held either horizontally or in other positions during measurement, and may have a tip portion that is substantially perpendicular to the major portion of the tool and maintains a constant length either at rest or at impact. The movement of the energy application tool, for example, a tapping rod, may be effected by a drive mechanism mounted inside the housing for driving the tapping rod from a substantially parallel position to the longitudinal axis of the housing to a position making an acute angle with the axis at a pivot point and back again, while the tip oscillates up and down in turn. Using this embodiment, measurements may be undertaken at locations which are relatively inaccessible such as, for example, in the molar area of a patient's teeth.

In one embodiment, the sleeve portion may attach and/or surround at least a length of the free end of the housing and protrudes from the housing for a distance substantially coextensive with the end of the energy application tool, for example, the tapping rod in its extended form if the tapping rod moves axially. Thus, the length of the sleeve portion in this embodiment may be somewhat dependent on the length of protrusion of the extended tapping rod desired. The free end of the sleeve may be placed against an object undergoing measurement. The contact by the sleeve portion on the object helps to stabilize the device on the object, as noted above. In another embodiment, the sleeve portion may be attached to the end of the housing and being substantially perpendicular to it when the energy application tool, for example, the tapping rod moves from being substantially parallel to making an acute angle with the longitudinal axis of the housing at a pivot when in operation. The sleeve portion may be substantially cylindrical in shape. In a further embodiment, the sleeve may be an extension of the housing and being of substantially a half cylindrical shape to allow the energy application tool, for example, the tapping rod to freely move when the tapping rod moves from being substantially parallel to making an acute angle with the longitudinal axis of the housing in operation. Using this system, measurements may be undertaken at locations which are relatively inaccessible such as, for example, in the molar area of a patient's teeth.

In another exemplary embodiment, the system described above may also include disposable features for aiding in eliminating or minimizing contamination of the object undergoing the measurement through transfer from the system or cross-contamination from previous objects undergoing the measurements, without interfering with the measurement or the capability of the system. The disposable feature may include any of those described below or as disclosed in U.S. publication no. 20130174639, entitled "System and Method For Determining Structural Characteristics Of An Object", the contents of which is hereby incorporated by reference in its entirety.

The present invention also relates to a system and method for measuring structural characteristics using an energy application tool and includes disposable features for aiding in eliminating or minimizing contamination of the object undergoing the measurement through transfer from the system or cross-contamination from previous objects undergoing the measurements, without interfering with the measurement or the capability of the system. The instrument includes a housing having a hollow interior with an open end and an energy application tool, for example, a tapping rod, or impact rod mounted inside the housing for movement inside the housing. The system provides a non-destructive method of measurement with some contact with the object undergoing such measurement without the need for wiping or autoclaving of the energy application tool, and at the same time without disposing of the energy application tool and/or the housing and whatever may be housed inside the housing of the instrument.

In one exemplary embodiment, the housing has a longitudinal axis and the energy application tool has a length with a resting configuration and an active configuration. The housing includes a sleeve portion extending therefrom. The sleeve portion is open at its free end, and has an object resting or contacting portion for resting on, pressing or contacting an object just prior and during measurement.

The energy application tool is driven by a drive mechanism. The drive mechanism may be an electromagnetic mechanism, and may include an electromagnetic coil and a permanent magnet secured to the back end of the energy application tool, for example, the tapping rod. The electromagnetic coil may lie axially behind the permanent magnet, for example.

In one embodiment, the resting configuration may be a retracted form and the active configuration may be an extended form and the energy application tool moves axially along the longitudinal axis of the housing, with the retracted form being retracted from the extended form. The movement of the energy application tool, for example, a tapping rod, may be effected by a drive mechanism mounted inside the housing for driving it axially within the housing between a retracted position and an extended position during operation. In the extended configuration, the free end of the energy tool may extend or protrude from the open end of the housing or sleeve portion, if one is present, and substantially extended to contact the object undergoing measurement. In one aspect, the instrument may be of any size including a size that enables measurements be undertaken at locations which are relatively inaccessible such as, for example, in the molar area of a patient's teeth.

In another embodiment, the resting configuration of the energy application tool may be a form that is substantially parallel to the longitudinal axis of the housing, and the active configuration may be a form making an acute angle with the longitudinal axis of the housing. Thus, during operation, the energy application tool oscillates from the substantially parallel position to the longitudinal axis of the housing to a position making an acute angle with the longitudinal axis of the housing about a pivot point. The energy application tool may be held either horizontally or in other positions during measurement, and may have a tip portion that is substantially perpendicular to the major portion of the tool and maintains a constant length either at rest or at impact. The movement of the energy application tool, for example, a tapping rod, may be effected by a drive mechanism mounted inside the housing for driving the tapping rod from a substantially parallel position to the longitudinal axis of the housing to a position making an acute angle with the axis at a pivot point and back again, while the tip oscillates up and down in turn. Using this embodiment, measurements may be undertaken at locations which are relatively inaccessible such as, for example, in the molar area of a patient's teeth. The disposable feature may include a covering for enveloping a part of the system that may come into proximity or contact with the object undergoing the measurement without interfering with the sensitivity, reproducibility, if desired, or general operation of the instrument to any substantial degree.

The covering may include a sleeve portion extending from and/or enveloping the open end of the housing. The sleeve portion includes a hollow interior and an open free end with an object resting or contacting portion for resting on, pressing or contacting an object during measurement at its open end. A feature such as a contact feature having a length and disposed towards the open end of the sleeve portion, fits snuggly inside the sleeve portion, for example, by friction. The contact feature may be, for example, a short tubular section, or a ring, and is adapted for freely moving or sliding inside the sleeve portion, substantially along the longitudinal axis of the sleeve portion, and may include a closed end for substantially closing the off the free end of the sleeve portion. The contact feature may be positioned in between the tip of the energy application tool and the surface of the object undergoing measurement and by being freely moving or sliding, may adjust itself to various surface configurations of an object undergoing measurement. The freely moving or sliding contact feature may vary in size and/or otherwise be adapted to move a desired predetermined distance along the longitudinal axis of the sleeve portion. In some examples, such as for a ring-shaped contact feature, movement stops, such as small ridges, stops or other obstacles, may be present inside the sleeve portion to prevent sliding or movement inside the sleeve portion outside of a desired range. For example, at least a portion of the closed end may be in the proximity of the surface of the object, and may or may not be in contact with the surface of the object just prior to impact by the energy application tool on the contact feature. During impact by the energy application tool on the closed end of the contact feature, at least a portion of the outside surface of the closed end or object contacting surface of the closed end of the contact feature is in close contact with the surface of the object. Thus, if at least at portion of the object contacting surface of the closed end is contoured to mirror the surface of the object it comes into contact with, the better contact with the object is made and energy transfer from the impact by the energy application tool may not be substantially impaired. In one aspect, the closed end of the contact feature may include at least a portion that may have a substantially flat portion facing the object to substantially mirror a flat surface of an object. In another aspect, the closed end of the contact feature may include at least a portion that may be contoured to mirror the surface of an object it comes into contact with if the object surface is contoured. For an example, if the surface of the object undergoing measurement includes a depression, the contact feature may include a closed end having a concave outside surface to substantially mirror the depression so as to adjust itself to maintain contact between the closed end and the object during impact. For another example, if the surface of the object includes a bump, the contact feature may include a closed end having a convex surface to substantially mirror the bump so as to maintain contact with the object during measurement. In a further aspect, the closed end may possess some elasticity or be deformable, so that close contact with the object may be achieved during impact.

In general, the contact between the object and at least a portion of the closed end of the contact feature, though the contact feature is freely moving, may nevertheless help to stabilize the device on the object and/or may improve the reproducibility of the measurements.

In one embodiment of the invention, during a measurement, the closed end of the contact feature may adjust itself to the surface configuration of the object and the object contacting portion of the open end of the sleeve properly contacts the object. The sensor described above, if present, senses and/or monitors that a proper contact force is exerted by the sleeve portion on the object. The energy application tool, for example, the tapping rod, taps the object indirectly through the closed end of the contact feature repeatedly during a measurement.

In another embodiment of the invention, during a measurement, the closed end of the contact feature adjusts itself to the surface configuration the object and the object contacting portion of the open end of the sleeve properly contacts the object, however, a portion of the closed end may extend beyond the sleeve to contact an irregular surface of the object simultaneously. The sensor described above, if present, senses and/or monitors that a proper contact force is exerted by the sleeve portion on the object. The energy application tool, for example, the tapping rod, taps the object indirectly through the closed end of the contact feature repeatedly.

The contact feature may be of any shape as long as it fits snuggly and yet freely moving or sliding inside the sleeve portion with a closed end substantially closing off the free end of the sleeve. It may be constructed of any material that may be molded or cast and may include polymers or filled polymeric material. For light weight, it may also be thin but of sufficiently stiffness to facilitate the sliding action.

The contact feature may also include a thin membrane at its closed end. The membrane may be attached or integrally bonded to the rest of the contact feature. The membrane may be chosen to have a minimal effect on the operation of the energy application tool. In one aspect, the membrane may possess some elasticity or deformability for better contact between the membrane and the object when struck by the energy application tool, as noted above, but may still be capable of transferring the impact force exerted by the energy application tool to the object. In another aspect, the membrane may be of any material that enables better transfer of impact force between it and the object.

In one embodiment, the closed end may include a thin polymeric membrane, which may or may not be of the same material as the rest of the contact feature, or it may be a material having substantially the same properties as the rest of the contact feature. The polymer may include any polymeric material that is capable of being molded, cast or stretched into a thin membrane so that it does not substantially adversely affect the measurement. In another embodiment, the closed end may include an insert molded metal foil membrane. The metal may be any metallic material that may be drawn, cast or molded into a thin membrane so that it does not substantially adversely affect the measurement. In other embodiments, the closed end may be integral to the contact feature. For example, the contact feature may be formed from a material which may be shaped into a tubular or ring structure with a closed end of a desired thickness, such as by stamping a metal (e.g. stainless steel, aluminum, copper, or other appropriate metal).

In another exemplary embodiment, the housing has a longitudinal axis and the energy application tool has a length with a resting configuration and an active configuration. The housing may or may not include a sleeve portion extending therefrom and has an open end at its free end.

In one embodiment of the invention, the resting configuration may be a retracted form and the active configuration may be an extended form when the energy application tool moves axially along the longitudinal axis of the housing, the retracted form being retracted from the extended form. The movement of the energy application tool, for example, a tapping rod, may be effected by a drive mechanism mounted inside the housing for driving it axially within the housing between a retracted position and an extended position during operation. In the extended configuration, the free end of the energy tool may extend or protrude from the open end of the housing, and substantially extended to contact the object undergoing measurement.

In another embodiment of the invention, the resting configuration of the energy application tool may be a form that is substantially parallel to the longitudinal axis of the housing, and the active configuration may be a form that makes an acute angle with the longitudinal axis of the housing. Thus, during operation, the energy application tool oscillates from the substantially parallel position to the longitudinal axis of the housing to a position making an acute angle with the longitudinal axis of the housing about the pivot point. The energy application tool may be held either horizontally or in other positions during measurement, and may have a tip portion that is substantially perpendicular to the major portion of the tool and maintains a constant length either at rest or at impact. The movement of the energy application tool, for example, a tapping rod, may be effected by a drive mechanism mounted inside the housing for driving the tapping rod from a substantially parallel position to the longitudinal axis of the housing to a position making an acute angle with the axis at a pivot point and back again, while the tip oscillates up and down in turn. Using this embodiment, measurements may be undertaken at locations which are relatively inaccessible such as, for example, in the molar area of a patient's teeth.

The disposable feature may include a covering for enveloping a part of the system that may come into proximity and/or contact with the object undergoing the measurement without interfering with the sensitivity, reproducibility, if desired, or general operation of the instrument to any substantial degree.

The covering may include a portion extending from and/or enveloping the open end of the housing, or the sleeve portion, if a sleeve portion extends from the housing. A contact feature having a length, and disposed towards the open end of the housing or sleeve portion may fit snuggly inside the housing or sleeve portion, by friction, and may extend beyond the open end of the housing or sleeve portion, if one is present. The contact feature includes a closed end for closing the free end of the housing or sleeve portion, if one is present. The closed end of the contact feature comes in between the tip of the energy application tool and the object, and a portion of the surface of the closed end of the contact feature comes into contact with at least a portion of the surface of the object undergoing measurement. In this exemplary embodiment, the end of the housing or sleeve portion may not come into contact with the object during measurement. The contact feature is adapted for be freely moving or sliding inside the housing or sleeve portion, if one is present, or may be slightly restricted to a predetermined distance of movement, and does not completely retract inside the housing or sleeve portion. The contact feature may include a closed end for substantially closing the free end of the housing or sleeve portion, if one is present. The stabilization of the device against an object undergoing measurement may be effected by the contact of at least a portion of the outside surface of the closed end of the contact feature on at least a portion of the surface of the object.

Here also, the contact feature is positioned in between the tip or end of the energy application tool and the surface of the object undergoing measurement and by being freely moving or sliding, may adjust itself to various surface configurations of an object undergoing measurement. For example, at least a portion of the closed end may be in contact with the surface of the object, prior to impact by the energy application tool on the contact feature. During impact by the energy application tool on the closed end of the contact feature, at least a portion of the outside or object contacting surface of the closed end remains in close contact with the surface of the object. Thus, if at least at portion of the object contacting surface of the closed end may be contoured to mirror the surface of the object it comes into contact with, the better contact with the object is made and energy transfer from the impact by the energy application tool may be not be impaired. In one aspect, the closed end of the contact feature may include at least a portion that may have a substantially flat portion facing the object to substantially mirror a flat surface of an object. In another aspect, the closed end of the contact feature may include at least a portion that may be contoured to mirror the surface of an object it comes into contact with if the object surface is contoured. For an example, if the surface of the object undergoing measurement includes a depression, the contact feature may include a closed end having a concave surface to substantially mirror the depression so as to adjust itself to maintain contact between the closed end and the object during impact. For another example, if the surface of the object includes a bump, the contact feature may include a closed end having a convex surface to substantially mirror the bump so as to maintain in contact with the object during measurement. In a further aspect, the closed end may possess some elasticity or may be deformable, so that close contact with the object may be achieved during impact.

For example, during a measurement, the closed end of the contact feature may adjust itself to the surface configuration of the object and stays in contact with the surface of the object. The energy application tool, for example, the tapping rod, taps the object indirectly through the closed end of the contact feature repeatedly.

The contact feature may be of any shape as long as it fits snuggly and yet free moving or sliding, for a predetermined length, if desired, inside the housing or sleeve portion, if one is present, with a closed end closing the free end of the housing or the sleeve portion, as discussed above. The contact feature may be of any appropriate length, such as, for example, a short tubular section, or a ring, and is adapted for freely moving or sliding inside the sleeve portion, substantially along the longitudinal axis of the sleeve portion, and may include a closed end for substantially closing the off the free end of the sleeve portion. The contact feature may be positioned in between the tip of the energy application tool and the surface of the object undergoing measurement and by being freely moving or sliding, may adjust itself to accommodate various surface configurations of an object undergoing measurement. The distance of movement for the contact feature may vary and in some instances may be of a predetermined distance. In some examples, such as for a ring-shaped contact feature, movement stops, such as small ridges, stops or other obstacles, may be present inside the sleeve portion to constrain the movement of the contact feature within the sleeve portion.

It may be constructed of any material that may be molded or cast and may include polymers or filled polymeric material. For light weight, it may also be thin but of sufficiently stiffness to facilitate the sliding action. The contact feature may include a thin membrane at its closed end such that it will not substantially affect the measurement. The membrane may be attached or integrally bonded to the rest of the contact feature. The membrane may be chosen to have a minimal effect on the operation of the energy application tool. In one aspect, the membrane may possess some elasticity or deformability for better contact between the membrane and the object when struck by the energy application tool, but still capable of transferring the impact force exerted by the energy application tool to the object. In another aspect, the membrane may be of any material that enables better transfer of impact force between it and the object.

In one embodiment, the closed end may include a thin polymeric membrane, which may or may not be of the same material as the rest of the contact feature, or it may be a material having substantially the same properties as the rest of the contact feature. The polymer may include any polymeric material that is capable of being molded, cast or stretched into a thin membrane so that it does not substantially adversely affect the measurement. In another embodiment, the closed end may include an insert molded metal foil membrane. The metal may be any metallic material that may be drawn, cast or molded into a thin membrane so that it does not substantially adversely affect the measurement. The membrane may also be formed to conform to the shape of the energy application tool, or vice versa, for optimal transfer of force/energy. In some exemplary embodiments, the membrane may be constructed from stainless steel foil or sheet, and may, for example, be stamped and/or molded. In other embodiments, the closed end may be integral to the contact feature. For example, the contact feature may be formed from a material which may be shaped into a tubular or ring structure with a closed end of a desired thickness, such as by stamping a metal (e.g. stainless steel, aluminum, copper, or other appropriate metal).

For these exemplary embodiments, the force sensor described above, including all aspects of its features, may or may not be present, for sensing and/or monitoring that a proper force is exerted by the object contacting portion of the sleeve portion or the closed end of the contact feature on the object, and/or for activating the system to start measurement when a proper force is exerted.

For a device of any of the exemplary embodiments described herein, having a force sensor for sensing or monitoring a force exerted by either the object contacting surface of the sleeve portion or the contact feature, the force sensor may be in physical proximity and/or contact with at least a portion of the device other than the energy application tool, for example, the sleeve portion or at least a portion of the sleeve portion, if the open end of the sleeve portion includes an object contacting portion, or at least a portion of the housing, if no sleeve portion is present.

The sensor, for example a force sensor, may be in physical proximity and/or contact and/or coupled with at least a portion of the device other than the energy application tool, for example, it may be in physical proximity and/or contact and/or coupled with the housing and/or sleeve portion, if the open end of the sleeve portion includes an object contacting portion, as noted above. The various embodiments of the sensor as described above are also applicable here.

Though the sensor is not physically or mechanically coupled to the energy application tool, it may be in electronic communication with the energy application tool and may act as an on/off switch for the device or instrument, as noted above. For example, when a proper force is exerted on the object by the object contacting portion of the sleeve, it may trigger the activation mechanism of the device or instrument to activate the movement of the energy application tool to start a measurement. Thus, no external switches or push buttons are needed to activate the on and off of the system, as noted above. The indication of the proper force may be indicated by visible or audible signals.

In one embodiment, the instrument may be instantaneously turned on once a proper contact force is exerted by the object contacting portion of the sleeve on the object, as indicated by visible or audible signals. In another embodiment, there may be a delay prior to turning on the instrument once a proper contact force is exerted by the object contacting portion of the sleeve on the object, as indicated by visible or audible signals. In a further embodiment, once a certain push force between the object contacting portion of the sleeve portion and the object is detected and maintained for a period of time, for example, about 0.5 seconds, the instrument may be turned on to start measurement. In this embodiment, a green light lights up the tip, and percussion will begin approximately 0.5 sec after a force in the correct range is maintained.

The proper force exerted by the operator on the object, for example, through the sleeve portion, acts as a switch of the system. When the system is not switched on, it may be desirable to know whether it has malfunction, not sufficient force or too much force is exerted. In one embodiment, the force measurement may be connected to a visual output, such as lights. Lights may be mounted at any convenient location on the device or instrument, for example, one or multiple LEDs may be mounted at the front of the device or instrument. In one aspect, a multiple light system may be included. For example, two LEDs may be used. When the force is in the correct range, the green light may be lit. If too much force is detected, the LEDs may change to red, and the instrument will not work unless the push force is reduced. In some embodiments, if the user is pushing too hard on the object, the light may change first to amber, then to red. If the push force is sufficient to change the light to red, percussion may either not be started, or be interrupted if it has already started. In addition, there may be an amber LED state which warns when the user is approaching too much push force. At that stage, the instrument may still operate when the LEDs are lit amber. In another aspect, no light may indicate too little force, a green light may indicate the right amount of force, while a red light may indicate too much force. In yet another aspect, a one light system may be included. For example, no light may give a signal of too little force and a red light may give a signal of too much force. In a further aspect, a flashing red light may indicate too much force and no light may indicate too little force.

In another embodiment, the force measurement may be connected to an audible output. In one aspect, the audible output may include a beeping sound to indicate too little force and a multiple beep to indicate too much force. In another aspect, the audible output may include a beeping sound to indicate too little force and a beeping sound with a flashing red light to indicate too much force. In a further aspect, the force measurement may be connected to a voice alert system for alerting too much force or too little force. In yet a further aspect, the force measurement may be connected to a voice alert system to alert too little force and a voice alert and a flashing red light for alerting too much force.

When the force sensor acts as an on/off switch, it may also act to monitor that a proper force is exerted by the object contacting portion of the sleeve portion during measurement and/or a proper alignment of the object contacting portion of the sleeve portion against the object during measurement is obtained. An inclinometer may be present, for example, as part of an electronic control system, which may trigger an audible warning when the device is outside of the angular range of operation, for example, for a tapping rod, it may trigger the warning when it is plus/minus 45 degrees, more for example, greater than about plus/minus 30 degrees from horizontal. If the device is oriented such that the axis of operation is greater than about plus/minus 45 degrees, more for example, greater than about plus/minus 30 degrees from horizontal when a push force is sensed on the object contacting portion of the sleeve portion, it may result in a warning sound being emitted by a speaker located on the device, such as the PCB within the device. In such circumstances, the percussion action will not begin until the device is returned to an acceptable angle. In some instances, if the percussion action has started when the above mentioned departure from the range is detected, the device may not actually stop operation, but may simply be sounding an alarm, so that corrections may be made.

The present invention further includes a disposable assembly having a sleeve portion adapted for attaching or coupling to a front portion of the device housing. The sleeve portion may include a front end and a back end and may include a coupling or mounting component towards its backend for coupling or attaching to the housing. In one embodiment, the mounting or coupling component may be friction fit, mating bayonet formations, tongue and groove type formations, snap fit, clips, internesting pin and pinhole formations, latches and other interconnecting structures onto a portion of the housing or parts inside the housing. In another embodiment, the mounting or coupling component of the sleeve and the housing may be a custom-made threaded system for better fit or coupling compatibility.

The disposable assembly of the present invention may be applicable to and/or may improve the reproducibility of measurement of any existing energy application tool, such as any percussion tool, in addition to aiding in eliminating or minimizing contamination or cross-contamination of the energy application tool or the object undergoing the measurement through transfer from the system or object, or cross-contamination from previous objects undergoing the measurements without the necessity of wiping and/or autoclaving the energy application tool prior to use. For example, for the system that includes an object contacting portion of a sleeve portion for contacting the object to be tested, or a feature for aiding in repositionability, for example, the systems and methods disclosed in U.S. Pat. Nos. 6,997,887, 7,008,385, and 9,358,089, the contents of all of which are hereby incorporated by reference in their entirety, the disposable feature aids in eliminating or minimizing contamination or cross-contamination of the energy application tool or the object undergoing the measurement through transfer from the system or object, or cross-contamination from previous objects undergoing the measurements without the necessity of wiping and/or autoclaving the energy application tool prior to use. For other examples, where the instruments do not include an object contacting portion of a sleeve portion, as disclosed in U.S. Pat. Nos. 4,482,324 and 4,689,011, the contents of which are incorporated herein by reference in their entirety, the disposable feature may transform them into systems that are capable of being reproducibly placed directly on the object undergoing such measurement for reproducible measurements and aiding in eliminating or minimizing contamination or cross-contamination of the energy application tool or the object undergoing the measurement through transfer from the system or object, or cross-contamination from previous objects undergoing the measurements without the necessity of wiping and/or autoclaving the energy application tool prior to use.

A contact feature freely sliding inside the sleeve portion may be disposed towards the front end of the sleeve portion of the disposable assembly. In one embodiment, the contact feature may be of any shape, for example, it may be of a short tubular section, and be of any dimension provided it is shorter than the length of the sleeve portion. It may include an open end and a closed end towards the front of the sleeve portion so that it substantially closed the front end of the sleeve portion. For it may be light weight, sufficiently thin but of sufficiently stiffness to facilitate the sliding action. In another embodiment, the contact feature may include a membrane attached to a ring. The ring may freely slide inside the sleeve portion and the membrane may substantially closed-off the opening of the housing or the sleeve portion, if one is present. The distance of movement for the freely moving or sliding contact feature may vary and in some instances may be of a predetermined distance. In some examples, such as for a ring-shaped contact feature, movement stops, such as small ridges, stops or other obstacles, may be present inside the sleeve portion to constrain the movement of the contact feature within the sleeve portion.

According to one embodiment, the sleeve portion may include an object contacting portion towards its front end for contacting a surface of an object undergoing measurement. In this embodiment, the sliding capability of the contact feature may not include any restraints as to distance and may freely sliding inside the sleeve portion. In this embodiment, the sleeve portion includes an object contacting portion towards its front end for contacting a surface of an object undergoing measurement.

According to another embodiment, the sleeve portion may not include an object contacting portion for contacting a surface of an object during measurement. In this embodiment, the sliding distance for the contact feature may be predetermined so that the front end of the contact feature may protrude further than the sleeve portion. The contact feature may be the component that provides the contact during measurement.

According to a further embodiment, the sleeve includes an object contacting portion towards its front end for contacting a surface of an object undergoing measurement and a tab extending substantially parallel to the longitudinal axis of the sleeve portion so that when the object contacting surface of the sleeve portion is in contact with at least a portion of a surface of the object undergoing the measurement, the tab may be resting on a portion or surface of the object that is different and is substantially perpendicular to the surface of the object in contact with the sleeve According to yet another embodiment, the sleeve portion includes a tab extending substantially parallel to the longitudinal axis of the sleeve portion so that when the object contacting surface of the contact feature is in contact with at least a portion of a surface of the object undergoing the measurement, the tab may be resting on a portion or surface of the object that is different and is substantially perpendicular to the surface of the object in contact with the contact feature.

According to still another embodiment, the sleeve portion may include a tab and a component, for example, a ridge, protrusion or other component substantially orthogonal to the surface of the tab on the side adapted for facing the surface of an object. For example, for teeth, the component may nest between adjacent teeth or other orthogonal surface and may thus aid in preventing any substantial lateral movement of the tab across the surface of the object and/or further aid in repeatability. The tab may be of sufficient length or width, depending on the length or width of the top portion of the object so that the ridge or protrusion may be properly located during operation.

In one embodiment, in addition to the disposable assembly having a mounting component or coupling component that may be friction fit, mating bayonet formations, tongue and groove type formations, snap fit, clips, internesting pin and pinhole formations, latches and other interconnecting structures onto a portion of the housing or parts inside the housing, additional features may be included in the device so that the activation mechanism of the device may not be triggered if the attached disposable assembly had been used before.

In another embodiment, in addition to the disposable assembly having a mounting component or coupling component that may be friction fit, mating bayonet formations, tongue and groove type formations, snap fit, clips, internesting pin and pinhole formations, latches and other interconnecting structures onto a portion of the housing or parts inside the housing, the mounting component may include a component that allows a predetermined number of connections made by the disposable assembly to the housing or parts inside the housing.

For the other embodiments of the device described herein, the device, for example, a percussion instrument, with or without any disposable feature, may also include a tab extending from the open end of the housing or sleeve portion so that the object contacting surface of the sleeve portion or contact feature described above is in contact with at least a portion of a surface of the object undergoing the measurement, the tab may be resting on a portion or surface of the object that is different and is substantially perpendicular to the surface of the object in contact with the sleeve or contact feature. The tab and the sleeve or contact feature together assists in the repeatable positioning of the device with respect to the object. In addition, the tab may be adapted for repetitively placed substantially at the same location on the surface of the object every time.

In one embodiment, the tab may be substantially parallel to the longitudinal axis of the housing or sleeve portion.

In another embodiment, the sleeve portion or housing may include a tab and a component, for example, a ridge, protrusion or other component substantially orthogonal to the surface of the tab on the side adapted for facing the surface of an object. For example, for teeth, the component may nest between adjacent teeth or other orthogonal surface and may thus aid in preventing any substantial lateral movement of the tab across the surface of the object and/or further aid in repeatability. The tab may be of sufficient length or width, depending on the length or width of the top portion of the object so that the ridge or protrusion may be properly located during operation.

For all the embodiment described herein, the component may be of any shape and size. In one aspect, for example, if the object is a tooth, the component may be short and of a sufficiently small thickness so that it may fit between adjacent teeth. In another aspect, for example, if the object is a tooth, the component may be short and shaped to fit between the top portion of adjacent teeth. In yet another aspect, for example, if the object is a tooth, and the component is to rest against the back surface, it may be of a dimension to cover a major portion of the back surface.

The tab and/or tab and component not only serve to aid in repeatable positioning of the instrument on an object, such as a tooth or mechanical or industrial structure, composites and similar, but the tab and/or tab and component also serve to help keep the object, such as a tooth or mechanical or industrial structure, composites and similar, as mentioned above, from moving in directions other than the direction parallel to the energy application or tapping direction. This helps to minimize any unnecessary disturbances of the object and/or the foundation it is anchored to and/or complications which may arise from these other disturbances during testing, thus further contributing to the sensitivity and/or accuracy of detection. The tab or the tab and/or component is applicable whether the sleeve portion has an object contacting portion or the contact feature provides the contact to the object.

The end of the sleeve not having the tab protruding from it may be flat or substantially flat and the part of the tab in contact with the top of the object may be also flat or substantially flat. The tab may extend in a substantially parallel direction from the end of the sleeve. In one aspect, the tab may be integral with the sleeve for a distance before protruding from the end of the sleeve, keeping substantially the cross-sectional outline of the sleeve after protruding from the sleeve. In another aspect, the tab may protrude uniformly from the top or bottom portion of the sleeve, but with a substantially different cross-sectional outline from that of the sleeve after protruding from the sleeve.

In one embodiment of the present invention, the tab may have a contact surface substantially mirroring the contour of the surface of an object to which it comes into contact during use for aiding in reproducibly positioning of the device directly on an object.

In one aspect, the protruding portion of the tab may have a rectangular cross-section. In another aspect, the protruding portion of the tab may have a slight arched top portion. In yet another aspect, the protruding portion of the tab may conform to the contour of the surface which comes into contact with the object.

In any of the embodiments, the corners of the tab are smooth or rounded or substantially smooth or rounded to avoid any catching on the object they may be resting on.

In general, the present device may be useful in making any measurements whereby vibration is generated through the application of energy, for example, the striking of, such as a tapping rod, on an object. The advantages are that the device may be held in contact with the object during the tapping action, in contrast to traditional devices that are not in contact.

The sleeve portion and the tab, and the feature and/or the sleeve, the tab and the contact feature, may be made of any material having vibration damping, acoustic damping, or vibration attenuating properties and the sleeve may be of such length so that any vibration traveling through the sleeve to the housing of the handpiece may be substantially attenuated. In one embodiment, the sleeve and the end of the housing adjacent to the sleeve may be made of the same material. In another embodiment, the sleeve and the end of the housing it is attached to may be made of materials having similar vibration attenuating properties. In yet another embodiment, the sleeve and the end of the housing it is attached to may be made of different materials. In a further embodiment, the sleeve and the end of the housing it is attached to may be made of materials having different vibration attenuating properties. In yet a further embodiment, the sleeve may be made of any material with a vibration attenuating coating on its surface or surfaces. In still yet another embodiment, the sleeve, tab and/or feature may be made of different materials having similar thermal expansion properties.

In addition, the sleeve portion, the contact feature and tab and/or the sleeve, the tab and the component, may be made of recyclable, compostable or biodegradable materials which are especially useful in those embodiments that are meant to be disposed of after one use.

The energy application tool is driven by a drive mechanism during measurement, as noted above. The drive mechanism may be an electromagnetic mechanism, and may include an electromagnetic coil. The drive mechanism may include a permanent magnet secured to the back end of the energy application tool, for example, the tapping rod, and the electromagnetic coil may lie axially behind this permanent magnet. In one embodiment, together with the back part of the housing, if the device is a handpiece, and any electrical supply lines, the magnetic coil forms a structural unit which may be integrally operational and which may be, for example, connected to the remaining device by a suitable releasable connection, for example, a screw-type connection or a plug-type connection. This releasable connection may facilitate cleaning, repairing and others. In another embodiment, the back part of the housing, if the device is a handpiece, and any electrical supply lines, the electromagnetic coil form a structural unit which may be integrally operational and which may be connected to the remaining device permanently. The energy application tool, such as the tapping rod, is located in the front part of the housing and the mounting mechanism for the tapping rod may include frictionless bearings. These bearings may include one or more axial openings so that the neighboring chambers formed by the housing and the tapping rod are in communication with one another for the exchange of air.

In one embodiment, the tapping rod may have a substantially constant cross-sectional construction over its entire length, with a permanent magnetic ensemble mounted at the end away from the free end, as noted above. The electromagnetic coil of the driving mechanism may be situated behind the same end of the energy application tool for example, the tapping rod as the permanent magnetic ensemble, resulting in a relatively small outside diameter for the housing. In this embodiment, the outside diameter of the housing may be substantially defined by the diameter of the electromagnetic coil, the cross-section of the energy application tool, such as the tapping rod, the mounting mechanism of the tapping rod in the housing, and the thickness of the walls of the housing. However, the length of the tool may be designed such that the electromagnetic coil (which represents the largest mass of the assembly) may be positioned to balance the device, for example, the handpiece in the hand, counterbalancing the batteries, if present, at the rear of the device.

The device itself may be tethered to an external power supply or be powered by an electrical source included inside the housing, such as, for example, a battery, a capacitor, a transducer, a solar cell, an external source and/or any other appropriate source.

In one embodiment, communication between the drive mechanism or portions of the drive mechanism, for example, the electronic control board part and the energy application tool, such as the tapping rod, may be via a lead or line of electrically conductive, insulated wire which may be wound spirally in a concentric fashion around the tapping rod and has spring-elastic properties. This may also allow a minimum space requirement with respect to the line management. The strand of wires wound concentrically around the rod connects the piezoelectric sensor to the control electronics. One purpose of concentrically winding the wire is to minimize the stress on the wire from repeated forward and back movement of the rod. In some embodiments, a helical spring, which may be formed by the spirally wound wire, may help to avoid or prevent looping or twisting of the wire connection.

In another embodiment, the communication between the drive mechanism and the energy application tool may be transmitted wirelessly via any suitable wireless connections. In one example, the energy application tool such as the tapping rod may be propelled forward by energizing the electromagnetic coil and creating a magnetic field that repels the magnet in the end of the tapping rod. The rod is retracted by reversing the polarity of the voltage applied to the electromagnetic coil. The magnet may also serve to hold the rod in its retracted position when the electromagnetic coil is not energized, through its magnetic attraction to the steel core of the coil.

A helical spring, if present, may be composed of stranded wires having two twisted individual wires or of a coaxial line. In its loaded condition, the spring may be compressed to such a degree that the force of its prestress corresponds to the frictional force and opposes this frictional force during the forward motion of the energy application tool, for example, the tapping rod from the retracted position to the extended position, or from a substantially parallel position to the longitudinal axis of the housing to a position making an acute angle with the axis at a pivot. The prestressed path of the spring may therefore be far greater than the stroke of the energy application tool, for example, the tapping rod so that spring power remains substantially constant over the entire stroke of the tapping rod. Any undesirable frictional force of the bearings of the mounting mechanism for the tapping rod during the forward motion may also be substantially compensated by this spring.

In one aspect, the drive mechanism may include a measuring device, for example, a piezoelectric force sensor, located within the housing for coupling with the energy application tool, such as the tapping rod. The measuring device is adapted for measuring the deceleration of the tapping rod upon impact with an object during operation, or any vibration caused by the tapping rod on the specimen. The piezoelectric force sensor may detect changes in the properties of the object and may quantify objectively its internal characteristics. Data transmitted by the piezoelectric force sensor may be processed by a system program, to be discussed further below.

In another aspect, the drive mechanism may include a linear variable differential transformer adapted for sensing and/or measuring the displacement of the energy application tool such as the tapping rod, before, during and after the application of energy. The linear variable differential transformer may be a non-contact linear displacement sensor. The sensor may utilize inductive technology and thus capable of sensing any metal target. Also, the noncontact displacement measurement may allow a computer to determine velocity and acceleration just prior to impact so that the effects of gravity may be eliminated from the results.

In one embodiment, the housing may be tapered towards the end surrounded by the sleeve portion so that the device may have a substantially uniform dimension when the sleeve is attached. In another embodiment, the housing may have a substantially uniform dimension and the sleeve may expand the dimension of the end it surrounds to a certain extent. In a further embodiment, the sleeve itself may have an inverse taper towards its free end to increase the flat area of contact with the object.

In general, the present device may be useful in making any measurements whereby vibration is generated through the application of energy, for example, the striking of, such as a tapping rod, on an object.

The evaluation of such structural characteristics mentioned above may be done in a number of methods, using a number of instruments, for example, a suitable instrument is as described in U.S. Pat. No. 6,120,466 ("the '466 patent"), issued 19 Sep. 2000 and entitled "System and Method for Quantitative Measurements of Energy Damping Capacity", incorporated herein by reference. Other instruments and methods may include such as those disclosed in U.S. Pat. Nos. 6,997,887, 7,008,385, and 9358,089, the contents of all of which are hereby incorporated by reference in their entirety. These measurements may include using an instrument to measure, for a time interval, energy reflected from the object as a result of the tapping or applying energy, which may include creating a time-energy profile based on the energy reflected from the object during the time interval, and/or evaluating the time energy profile to determine the damping capacity of the object. Further device may also be used, such as that disclosed U.S. Pat. Nos. 4,482,324 and 4,689,011, incorporated herein by reference in their entirety. All these instruments and devices may be modified with the present disposable assembly for aiding in eliminating or minimizing contamination of the object undergoing the measurement through transfer from the system or cross-contamination from previous objects undergoing the measurements, without interfering with the measurement or the capability of the system and with added repetitive repositionability.

In general, the structural characteristics as defined herein may include vibration damping capacities; acoustic damping capacities; defects including inherent defects in, for example, the bone or the material that made up the object; cracks, micro-cracks, fractures, microfractures; loss of cement seal; cement failure; bond failure; microleakage; lesions; decay; structural integrity in general or structural stability in general. For an anatomical object, such as a tooth structure, a natural tooth, a natural tooth that has a fracture due to wear or trauma, a natural tooth that has become at least partially abscessed, or a natural tooth that has undergone a bone augmentation procedure, a prosthetic dental implant structure, a dental structure, an orthopedic structure or an orthopedic implant, such characteristics may indicate the health of the object, or the health of the underlying foundation to which the object may be anchored or attached. The health of the object and/or the underlying foundation may also be correlated to densities or bone densities or a level of osseointegration; any defects, inherent or otherwise; or cracks, fractures, microfractures, microcracks; loss of cement seal; cement failure; bond failure; microleakage; lesion; or decay. For objects in general, for example, polymeric composite structures including honeycombs or layered honeycombs or metallic composite structure; an airplane structure, an automobile, a ship, a bridge, a building, industrial structures including, but not limited to power generation facilities, arch structures, or other similar physical structures; such measurements may also be correlated to any structural integrity, or structural stability, such as defects or cracks, even hairline fractures or microcracks and so on.

Additionally, changes in the structure of the tooth that reduce its ability to dissipate the mechanical energy associated with an impact force, and thus reduce overall tooth structural stability, can be detected by evaluation of the energy return data as compared to an ideal non-damaged sample. In addition, as noted above, the present invention also contributes to the accuracy of the location of detection of defects, cracks, micro-cracks, fractures, microfracture, leakage, lesions, loss of cement seal; microleakage; decay; structural integrity in cement failure; bond failure; general or structural stability in general.

The present invention further relates to a system and method for measuring structural characteristics that minimizes impact, even minute impact on the object undergoing measurement, without compromising the sensitivity of the measurement or operation of the system. In one embodiment, the system includes an energy application tool that is light weight and/or capable of moving at a slower velocity such that it minimizes the force of impact on the object during measurement while exhibits or maintains better sensitivity of measurement. In one aspect, the energy application tool, for example, the tapping rod, may be made of lighter material to minimize the weight of the handpiece, if the device is a handpiece. In another embodiment, the energy application tool, for example, the tapping rod, may be made shorter and/or of smaller diameter such that the size of the handpiece may also be minimized. In a further embodiment, the system may include a drive mechanism that may lessen the acceleration of the energy application tool. For example, the drive mechanism may include a smaller drive coil to lessen the acceleration of the energy application tool, whether or not it is light weight, and/or smaller in length or diameter, and the impact force on the object during operation while maintaining sensitivity of measurement. These embodiments may be combined with one or more of the embodiments described before, including the lighter weight handpiece housing. The speed of conducting measurement may also be desirable without increasing the initial velocity of impact so as to minimize impact on the object during measurement. The present invention relates to yet another system and method for measuring structural characteristics having a drive mechanism that may decrease the travel distance of the energy application tool, for example, from about 4 mm to about 2 mm, while maintaining the same initial velocity at contact and thus, faster measurement is possible without compromising the operation of the system. The system may or may not have disposable parts and/or features for aiding in repositionability and/or lessening impact with features mentioned below.

As noted above, the device may be tethered to an external power supply or be powered by an electrical source included inside the device housing. If powered by an electrical source inside the device housing, the power source may or may not be rechargeable. If rechargeable, a base charging station may be used. The base station may be a separate independent station or it may be part of the system of the present invention. For an independent charging station, any existing station may be applicable. The charging mechanism may be wired or wireless. For these charging base, only electrical current to charge the device is provided in most instances. For a base station that may be part of the system, more than electrical current to charge the device may be provided.

The present invention still further relates to a base station that may be part of the system of the present invention and may be plugged into the computer, for example, a PC via a USB cable. This connection may provide both data transfer between the PC and the base station, and electrical current to charge the device during the charging process when the device is docked. In this way, the base station may also serve to act as a wireless transceiver for the PC in the communication with the wireless transceiver in the device.

It may be desirable for each device to be accompanied by its own charging base station. This may avoid the possibility of the wrong device communicating with the wrong base station, in a multiple device environment. This may be important in any testing setting, for example, a dental office.

During preparation of the system just prior to performing a measurement on an object, the device is docked in the charging base to pair that device with that base station as part of the usage protocol, for example, prior to starting a patient testing session in a dental office. The usage protocol may be controlled by the software.

For the embodiments where the device may be equipped with a disposable feature or assembly described above, the disposable portion is generally removed from the device prior to placing the device in the charging base. In other embodiments, the disposable portion may be physically accommodated in the interface between the device and the base.

The present invention yet further relates to a non-reusable and disposable assembly or feature in a healthcare setting. As noted above, the disposable feature or assembly is for aiding in eliminating or minimizing contamination of the object undergoing the measurement through transfer from the system or cross-contamination from previous objects undergoing the measurements, without having to carry out a decontaminating process prior to moving to a different test object. To ensure that such features or assemblies once used are not reused, the disposable features or assemblies may be programmed to be one use. In one embodiment, a computer chip may be used. The chip may be present on a PCB located on the disposable feature or assembly, for example, in the back of the disposable assembly, may serves to ensure that once used, it cannot be or is not reused, so that any unwanted material may not be transferred from one patient to another. When a disposable feature or assembly is coupled to the device, the chip in the assembly or feature is interrogated by the device with a challenge and response system to ensure authenticity, Once authenticated, it is permanently marked as 'used'. If a used assembly or feature is placed on the device again, whether it is the same device or a different one, the challenge and response will fail, and the device will not be able to function as intended. In another embodiment, a timeout function may also be used to prevent the reuse of the disposable assembly or feature after a certain period of coupled time. In a further embodiment, the chip as well as the timeout function may be used for further insurance. In yet a further embodiment, the attachment mechanism of the disposable feature or assembly may include a part that once removed from the device is either snapped off or is warp to render it no longer attachable to a device.

To further facilitate the ease of use of the system, better lighting of the object undergoing measurement may be provided, such as with light pipes or other illumination which may be used to enable better lighting of the object and enhance the visualization by the user. In some embodiments, the light pipes may also be utilized to aid in coupling between components, such as between the handpiece and the disposable feature.

The present invention together with the above and other advantages may best be understood from the following detailed description of the aspects, embodiments and examples of the invention and as illustrated in the drawings. The following description, while indicating various aspects, embodiments and examples of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE DRAWINGS

FIG. 1 illustrates a block diagram of a device in embodiments of the present invention;

FIGS. 1a and 1b illustrate perspective views of a handpiece with sleeve portions in embodiments of the invention;

FIG. 1c illustrates the end of a handpiece without a sleeve portion;

FIG. 1f illustrates a block diagram of a device with a substantially perpendicular sleeve portion and a pivoting energy application tool;

FIG. 3 illustrates contact of a sleeve portion with objects with an irregular surface with a convex portion;

FIG. 3a illustrates contact of a sleeve portion with objects with an irregular surface with a concave portion;

DETAILED DESCRIPTION OF THE INVENTION

Figure 1G:
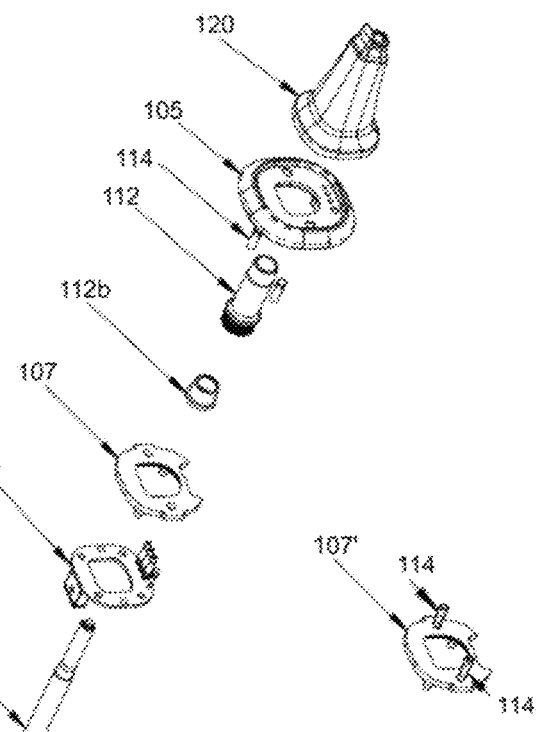
FIG. 1g illustrates an alternative configuration for lighting features.

The detailed description set forth below is intended as a description of the presently exemplified systems, devices and methods provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplary methods, devices and materials are now described.

All publications mentioned herein are incorporated herein by reference for the purpose of describing and disclosing, for example, the designs and methodologies that are described in the publications which might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

The present invention may be used to test objects of practically any size and shape, to obtain information on their structural characteristics. The measuring device may come in any sizes also, for example, it may be a handpiece useful for testing objects that may be difficult to measure with usual tools. The system may be used to conduct non-destructive measurements. Such structural characteristics not only include the physical characteristics of an object or the foundation the object may be anchored to, but also information as to their locations, compatibility or suitability of a material for use in dental work prior to the actual work, whether a tooth structure is restorable prior to the actual work, whether a restorative procedure is successful, when the tooth structure that underwent any procedure has been remodeled, the looseness of tooth structure before and after dental work, and combinations thereof.

As mentioned above, the system and method of the present invention is a non-destructive method. This is applicable to a system that may or may not have disposable parts and/or features for aiding in repositionability. As noted above, the device may be part of a system that includes computerized hardware and instrumentation software that may be programmed to activate, input and track the action and response of the device for determining the structural characteristics of the object. The hardware may include a computer for controlling the device and for analyzing any data collected, for example, the deceleration of the energy applying tool, for example, the tapping rod, upon impact with an object. In general, the device and hardware may communicate via wired connection(s), wireless connection(s) and/or a combination. Upon activation, the energy application tool, for example, the tapping rod extends at a speed toward an object and the deceleration of the tapping rod upon impact with the object may be measured by a measuring device, for example, a piezoelectric force sensor, installed in the device, and transmitted to the rest of the system for analysis. In one aspect, the tapping rod may be programmed to repeatedly strike an object, for example, a certain number of times per second or minute at substantially the same speed and the deceleration information is recorded or compiled for analysis by the system. In some embodiments, the object may be struck 4 times per second.

In general, the object may be subjected to an energy application processes provided via a device, for example, a handpiece, which forms a part of a computerized system capable of collecting and analyzing any data animating from the object. As noted above, many different structural characteristics may be determined using the system and methods of the present invention, including vibration damping capacities, acoustic damping capacities, structural integrity or structural stability of both mechanical and anatomical objects and any foundations they may be anchored thereon, as noted above. For an anatomical object, such as a tooth, natural or restored, prosthetic dental implant structure, a dental structure, or an orthopedic implant, examples of the structural characteristics as defined herein may include vibration damping capacities, acoustic damping capacities, or structural stabilities and may indicate the health of the object. The health of the object, may also be correlated to bone densities or a level of osseointegration; structural integrity such as defects or cracks, noted above. For objects in general, such measurements may also be correlated to their structural integrity such as defects or cracks, also a noted above. For a physical structure, such as a plane, an automobile, a ship, a bridge, a building or other similar physical structures or damping material suitable to aid in the construction of such structures, examples of the structural characteristics as defined herein may include vibration damping capacities, acoustic damping capacities, or structural stabilities and may indicate the health of the structural integrity of the object.

The present invention provides an effective and repeatable measurement of the structural characteristics of an object, mentioned above and/or below.

The instrument of the present invention may be used to such purposes and may be useful to predict the suitability of a material prior to construction in addition in for example, an anatomical object, to detection of loss of cement seal; cement failure; bond failure; microleakage; decay and so on after the construction, as mentioned above. In addition, the present invention is useful in distinguishing between defects inherent in the material making up the structure or object, and cracks or fractures as discussed above due to trauma or wear or repeated loadings. Defects inherent in the bone or material construction of an implant, or a physical structure, for example, may include lesions in the bone, similar defects in the implant construction or polymer, polymer composites or alloys, any type of ceramics, or metallic composites or alloys. For example, in measuring the damping characteristics of teeth, whether natural or restored, dental implant structures, orthopedic implant structures, and a variety of other applications where the measurement of damping characteristics is utilized, including, but are not limited to, testing airplane structures, composite structures, engineering materials, or the secureness of medical implants, and is particularly advantageous in locations that were difficult to access or where liquid couplants could not be used. Structural integrity, such as the looseness of a screw, cracks in teeth as well as bone and bone voids, debonded restorations, and damage in integrated circuit materials may also be measured. However, the above list is not intended to be exhaustive.

In one aspect of the invention, the system may include an instrument which houses an energy application tool for generating an applied force on an object, such as through physical impact, percussion or repeated tapping impact, and a sensing mechanism for detecting characteristics of the resulting applied force, such as, for example, the deceleration of the energy application tool upon impact, energy back-propagated from the impact, physical deformation of the energy application tool, and/or any other appropriate characteristic or combination thereof.

Figure 1D:
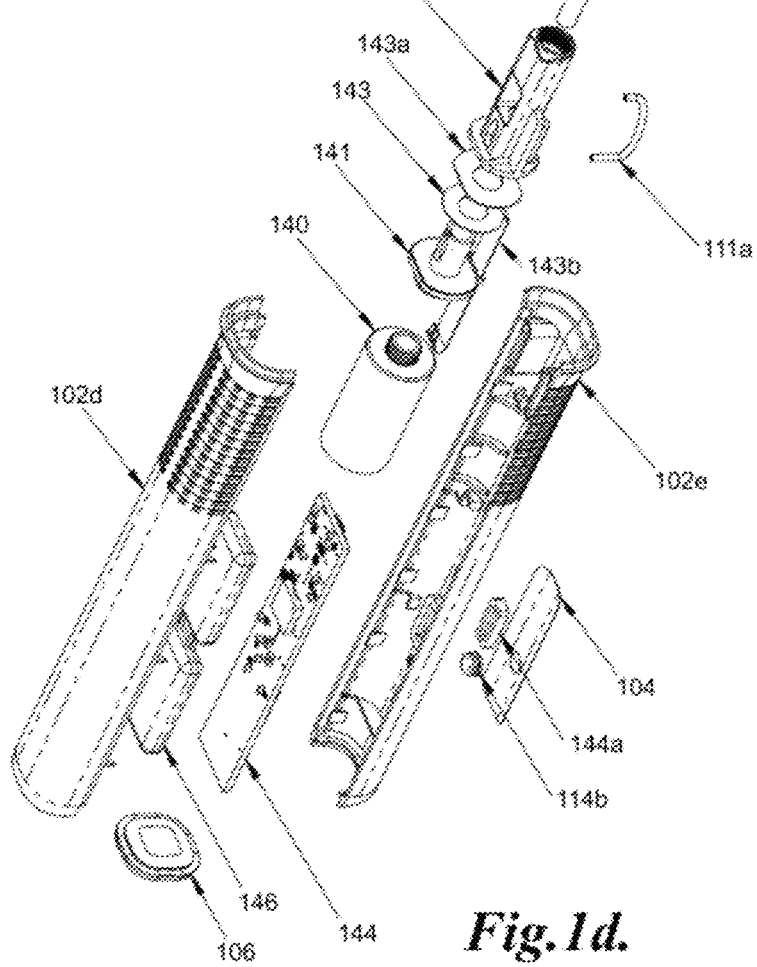
FIG. 1d illustrates an exploded view of a handpiece with a sleeve portion.
Figure 1E:
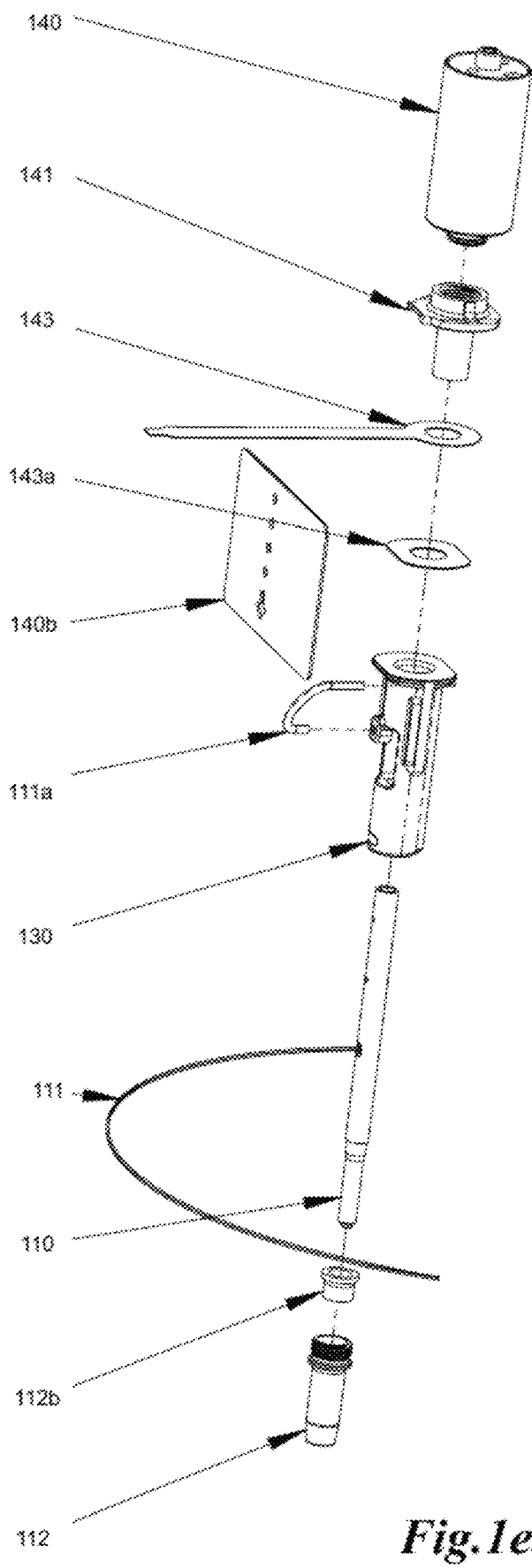
FIG. 1e illustrates an exploded view of a portion of a handpiece showing portions of the drive mechanism, a force sensor and a piezoelectric sensing wire without a sleeve portion shown.

In exemplary embodiments, the instrument may include a handpiece 100 having a housing 102 which houses the energy application tool and sensing mechanism, as illustrated in the block diagram of FIG. 1 and the exploded view of FIG. 1d. In general, a handpiece may refer to a handheld device, but may also include, without limitation, any other appropriate form for the desired application, such as mounted devices or tool/mechanically/robotically articulated devices. The handpiece 100 may also be referred to, for example, as a device or instrument interchangeably herein. In some embodiments, the energy application tool 110, as illustrated, may be mounted within the housing 102 for axial movement in the direction A toward an object, and such axial movement may be accomplished via a drive mechanism 140. Drive mechanism 140 may generally be a linear motor or actuator, such as an electromagnetic mechanism which may affect the axial position of the energy application tool 110, such as by producing a magnetic field which interacts with at least a portion of the energy application tool 110 to control its position, velocity and/or acceleration through magnetic interaction. For example, an electromagnetic coil disposed at least partially about the energy application 110 may be energized to propel the energy application tool 110 forward toward the object to be measured, as illustrated with the electromagnetic coil 140, which may be retained by a wrapping 140b, as illustrated in the exploded view of FIG. 1e. The electromagnetic coil may also, for example, be alternatively energized to propel the energy application tool 110 backward to prepare for a subsequent impact. Other elements, such as rebound magnetic elements, may also be included, such as to aid in repositioning of the energy application tool 110 after propelling via the electromagnetic coil. The drive mechanism 140 and/or other portions of the instrument may generally be powered by a power source, as shown with power source 146, which may be a battery, capacitor, solar cell, transducer, connection to an external power source and/or any appropriate combination. An external connection to a power source, either to power the handpiece 100 or to charge the internal power source, such as the power source 146, may be provided, such as a power interface 147 in FIG. 1, which may include, for example, a power contact 113a as in FIGS. 1c and 1d for direct conductive charging, or the power interface 147 may utilize wireless charging, such as inductive charging.

In some other embodiments, the energy application tool 110 may be utilized to move substantially in a direction A which may be perpendicular or substantially perpendicular to the longitudinal axis of the housing 102, as illustrated in the block diagram of a handpiece 100 in FIG. 1f. As illustrated, the energy application tool 110 may, for example, be substantially L-shaped to accommodate the interaction with the drive mechanism 140 and protrude in direction A, substantially perpendicular to the axis of the housing 102. As illustrated in an example, the drive mechanism 140 may act on the energy application tool 110 to cause it to rock on a pivot 110a, causing it to move in direction A at its tip. The drive mechanism 140 may utilize, for example, an alternating magnetic element which may act on the energy application tool 110 to cause it to move alternatingly in two directions, such as up and down. In another example, the bend portion of the L-shaped energy application tool 110, such as shown with bend 110b, may include a flexing and/or deformable construction such that a linear force applied by the drive mechanism 140 may push the energy application tool 110 in the direction A at the tip by conveying the forward motion around bend 110b. For example, the bend 110b may include a braided, segmented, spring-like and/or otherwise bendable section that may also convey motion and/or force around a bend.

In exemplary embodiments, the energy application tool 110 may generally include a tapping rod or impact rod, as illustrated in FIGS. 1, 1d and 1e with the linear rod-shaped energy application tool 110. In general, portions of the energy application tool 110 may be designed for delivery of the desired amount of energy, such as via impact, to the object and/or for carrying return energy for measurement. The energy application tool 110 may further be designed to interact with the drive mechanism 140, such as by including metallic, magnetic (e.g. ferromagnetic), conductive and/or other desirable portions or components, such as those that may be manipulated by magnetic fields and forces. The energy application tool 110 may also be designed, for example to decrease its overall mass or density, such as for easier propulsion by the drive mechanism 140 and/or for controlling the force of impact on the object.

To aid in the movement of the energy application tool 110, such as a tapping or impact rod, a support or bearing may be utilized that the energy application tool 110 may slide freely in, but is constrained from moving off axis, as shown with slide retainer 112b in FIGS. 1d and 1e.

In exemplary embodiments, the handpiece 100 may further house a sensing mechanism 111 for detecting characteristics of the effects from the impact of the energy application tool 110 with the object. In general, the sensing mechanism 111 may be physically coupled to, functionally coupled to or otherwise in contact with the energy application tool 110 such that it may detect characteristics of the impact. In some embodiments, the sensing mechanism 111 may include a piezoelectric sensing element which may generally produce an electrical signal or change in response to mechanical energy, such as a change in pressure on the piezoelectric sensing element, may be utilized for analysis of the object. A piezoelectric wire may, for example, be loaded into the energy application tool 110, as shown with the sensing mechanism 111 being inserted in FIG. 1e. The sensing mechanism 111 may also include other forms of sensing elements, such as, for example, a linear variable differential transformer which may sense the position of the energy application tool 110 due to changes in voltage in the transformer due to positioning of the energy application tool 110 which may be metal or otherwise affect the induction in the transformer, accelerometers, resistive pressure sensors, strain gauges, and/or any other appropriate type of sensor or combination of sensors. In general, the position of the sensing mechanism 111 or portions thereof may be determined for optimal sensing of the desired characteristic. For example, a piezoelectric sensing element may generally be placed as close to the point of impact as practicable, such as near the tip that impacts the object, such that a greater amount of physical deformation of the energy application tool 110 may be detected. The sensing mechanism 111 may be adapted for measuring the deceleration of the energy application tool 110 upon impact with an object during operation, or any vibration caused by the impact. The sensing mechanism 111 may detect changes in the properties of the object and may quantify objectively its internal characteristics. Data transmitted by the sensing mechanism 111 may be processed by a system program, to be discussed further below.

In some embodiments, communication between the drive mechanism 140 or portions of the drive mechanism, for example, the energy application tool 110, the sensing mechanism 111 or the electronics assembly 144 may be via a lead or line of electrically conductive, insulated wire which may be wound spirally in a concentric fashion around the tapping rod and has spring-elastic properties. This may also allow a minimum space requirement with respect to the line management. For example, a strand of wires wound concentrically around the energy application tool 110 may be utilized to carry signals to and/or from the sensing mechanism 111. One purpose of concentrically winding the wire is to minimize the stress on the wire from repeated forward and back movement of the energy application tool 110. In some embodiments, a helical spring, which may be formed by the spirally wound wire, may help to avoid or prevent looping or twisting of the wire connection.

In another embodiment, the communication between the drive mechanism 140 and the energy application tool 110 may be transmitted wirelessly via any suitable wireless connections. In one example, the energy application tool 110, such as the tapping rod may be propelled forward by energizing the electromagnetic coil and creating a magnetic field that repels the magnet in the end of the energy application tool, for example, the tapping rod. The rod is retracted by reversing the polarity of the voltage applied to the electromagnetic coil. The magnet may also serve to hold the rod in its retracted position when the electromagnetic coil is not energized, through its magnetic attraction to the steel core of the coil.

A helical spring, if present, may be composed of stranded wires having two twisted individual wires or of a coaxial line. In its loaded condition, the spring may be compressed to such a degree that the force of its prestress corresponds to the frictional force and opposes this frictional force during the forward motion of the energy application tool, for example, the tapping rod from the retracted position to the extended position, or from a substantially parallel position to the longitudinal axis of the housing to a position making an acute angle with the axis at a pivot. The prestressed path of the spring may therefore be far greater than the stroke of the energy application tool, for example, the tapping rod so that spring power remains substantially constant over the entire stroke of the tapping rod. Any undesirable frictional force of the bearings of the mounting mechanism for the tapping rod during the forward motion may also be substantially compensated by this spring.

The handpiece 100 may include features, such as in the electronics assembly 144, which may generally control the drive mechanism 140 and may also store, process and/or transmit data from the sensing mechanism 111. The electronics assembly 144 may include, for example, wired or wireless transmission features to relay data to a computer or other device for analysis or viewing. In some embodiments, the electronics assembly 144 may interface with an outside device, such as via electronics contacts 113 in FIG. 1c, to transmit data.

As illustrated in FIGS. 1d and 1e, the sensing mechanism 111 may connect to the electronics assembly in a wired manner, such as through a wired connection carried in a conduit 111a, which may be flexible, for example, to accommodate the movement of the energy application tool 110. The conduit 111a may also provide protection to the wired connection from moving components in the handpiece 100, such as the energy application tool 110.

As noted above, the handpiece 100 may be tethered to an external power supply or be powered by an electrical source included inside the housing 102, such as the power source 146. If powered by an electrical source inside the housing 102, the power source 146 may or may not be rechargeable. If rechargeable, a base charging station may be used.

Figure 5:
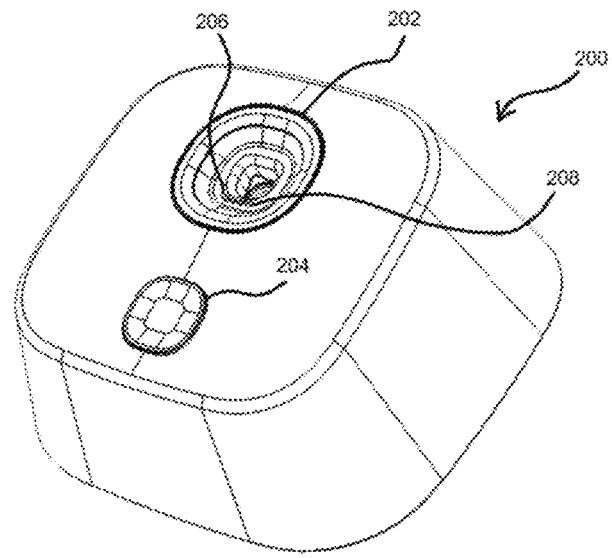
FIGS. 5 and 5a illustrate a base unit for a handpiece.
Figure 5A:
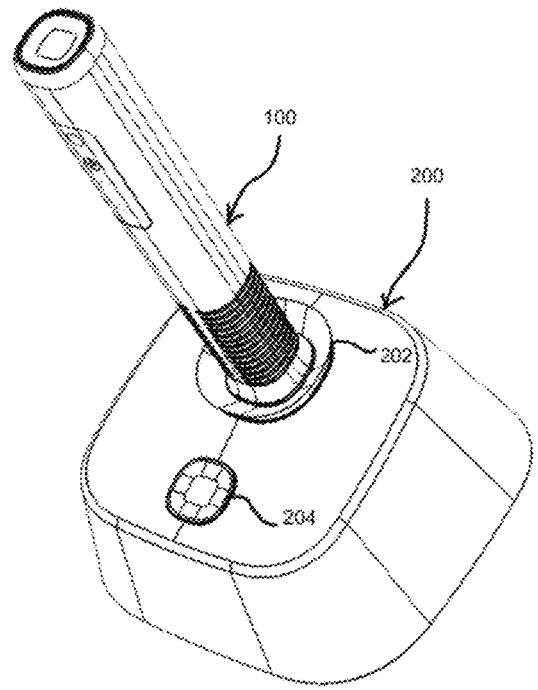

FIGS. 5 and 5a illustrate a base station 200 which contains a handpiece receptacle 202 for receiving the handpiece 100. The base station 200 may be a separate independent station or it may be part of the system of the present invention. For an independent charging station, any existing station may be applicable. The charging mechanism may be wired or wireless. For these charging base, only electrical current to charge the device may be provided. For a base station that may be part of the system, more than electrical current to charge the device may be provided.

The present invention still further relates to a base station that may be part of the system of the present invention and may be plugged into the computer, for example, a PC via a USB cable. This connection may provide both data transfer between the PC and the base station, and electrical current to charge the device during the charging process when the device is docked. In this way, the base station may also serve to act as a wireless transceiver for the PC in the communication with the wireless transceiver in the device.

FIG. 5 illustrates an example of a base station 200 with base electronics contacts 206 which may contact and transfer data through corresponding contacts on the handpiece 100, such as the electronics contacts 113. The base station 200 may further supply charging to the handpiece, such as through base power contact 208, which may charge by contact with a corresponding feature on the handpiece 100, such as power contact 113a.

It may be desirable for each device to be accompanied by its own charging base station. This may avoid the possibility of the wrong device communicating with the wrong base station, in a multiple device environment. This may be important in any testing setting, for example, a dental office. For example, each handpiece 100 may have an accompanying base station 200.

During preparation of the system just prior to performing a measurement on an object, the handpiece 100 may be docked in the base station 200 to pair that device with that base station 200 as part of the usage protocol, for example, prior to starting a patient testing session in a dental office. The usage protocol may be controlled by the software. The pairing may also be accomplished by placing a base station 200 and a handpiece 100 into a pairing mode, such as via controls 204 and/or a programming button 144a as shown in FIG. 1d, 5 and 5a.

For the embodiments where the device may be equipped with a disposable feature or assembly described above, such as a sleeve 120, the disposable portion is generally removed from the device prior to placing the device in the base station 200. In other embodiment, the disposable portion may be physically accommodated in the interface between the device and the base station 200.

In some exemplary embodiments, the handpiece 100 may include a housing with a hollow interior with an open end, as illustrated in FIGS. 1a, 1b and 1c with housing 102, applicator end 102a with aperture 102c and distal end 102b. In general, the energy application tool 110 or at least a portion thereof may emerge from an opening in the housing 102, as shown in FIG. 1c with aperture 102c. The housing 102 may also include handling features, such as gripping features 103 as illustrated. The housing 102 may also include other features such as to access portions of the interior, such as battery access cover 104.

The housing 102 may include multiple portions or parts, such as illustrated in FIG. 1d with upper and lower housing clamshells 102d, 102e, forward end cap 105, and base end cap 106. In general, the components of the handpiece 100 may be arranged within the housing 102, such as substantially axially arranged with the energy application tool 110 forming the approximate center of the formation with other components concentrically arranged.

The forward end cap 105 may include apertures for portions of the device to emerge, such as the aperture 102c to allow the energy application tool 110 and/or its associated components to emerge.

In another aspect of the invention, the system may include features for aiding the stable, consistent and/or reproducible positioning of the energy application tool 110 relative to an object to be measured, which may also be conducted in a manner that reduces cross-contamination or other sanitization issues.

In some exemplary embodiments, a sleeve portion as discussed above and/or below may be included that may be present or positioned near the portion of the energy application tool 110 that contacts and/or impacts the object and utilized in conjunction with the handpiece 100 and associated components discussed above. FIGS. 1, 1a, 1b and 1d illustrate a sleeve 120 disposed near the applicator end 102a of the housing 102. In some embodiments, the sleeve portion, such as the sleeve 120 may be integral to the handpiece 100 or mounted to the handpiece 100 in a permanent or semi-permanent manner, such as for multiple uses. The sleeve portion may also be a removable and/or disposable piece which may be replaced, such as between different patients and/or procedures to aid in reducing cross-contamination or other sanitization issues, such as the need to sanitize/sterilize the portions of the system that contact a patient.

Figure 2:
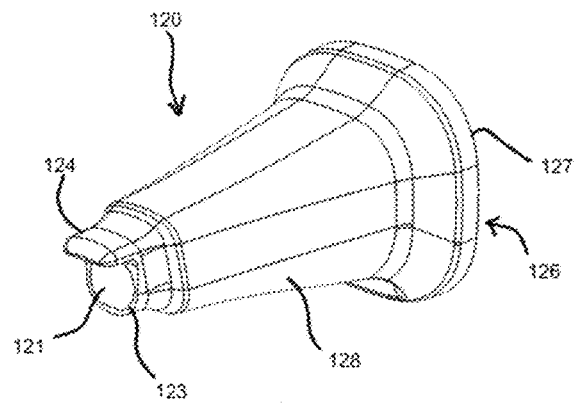
FIG. 2 illustrates a sleeve portion with a tab.
Figure 2A:
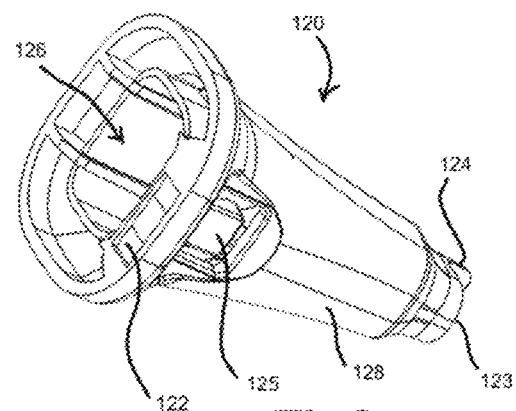
FIG. 2a illustrates a sleeve portion with a security feature and an attachment feature.

FIGS. 2, 2a, 2b and 2c illustrate embodiments of the sleeve 120 which are separable pieces from the rest of the handpiece 100. The sleeve 120 may generally couple to the handpiece 100 or portion thereof through any appropriate form of connection, such as, for example, any threaded attachment, friction fit, mating bayonet formations, tongue and groove type formations, snap fit, clips, internesting pin and pinhole formations, latches and other interconnecting structures. FIGS. 1b and 2a illustrate a clip 125 on the sleeve 120 which may clip onto a portion of the handpiece 100, such as the sleeve mount 112a in FIGS. 1c and 1d.

In one embodiment of the invention, the sleeve portion, such as the sleeve 120, may be a non-reusable and disposable assembly or feature in a healthcare setting, such as a dentistry office or similar. As noted above, the disposable feature or assembly is for aiding in eliminating or minimizing contamination of the object undergoing the measurement through transfer from the system or cross-contamination from previous objects undergoing the measurements, without having to carry out a decontaminating process prior to moving to a different test object. To ensure that such features or assemblies once used are not reused, the disposable features or assemblies may be programmed to be one use. In some embodiments, a computer chip may be used. The chip may be present on a PCB located on the disposable feature or assembly, for example, in the back of the disposable assembly, may serves to ensure that once used, it cannot be or is not reused, so that any unwanted material may not be transferred from one patient to another. FIGS. 1 and 2a illustrate a device coupled to the sleeve 120 which may be utilized to interface with the electronics of the handpiece 100, such as via electronic interface 142, which may utilize contact pins such as electronic contacts 113 in FIG. 1c, or other forms of electronic interface, such as Radio Frequency ID (RFID), Near Field Communication (NFC), Bluetooth, and/or any other appropriate form of interface.

The electronic interface 142 may include a PCB, such as illustrated with sleeve mount PCB 108 and its retainer 107 in FIG. 1d. The electronic contacts 113, if utilized, may emerge from the housing 102 through apertures in the forward end cap 105.

When a disposable feature or assembly is coupled to the device, the chip in the assembly or feature is interrogated by the device with a challenge and response system to ensure authenticity. Once authenticated, it is permanently marked as 'used', If a used assembly or feature is placed on the device again, whether it is the same device or a different one, the challenge and response will fail, and the device will not be able to function as intended. In another embodiment, a timeout function may also be used to prevent the reuse of the disposable assembly or feature after a certain period of coupled time. In a further embodiment, the chip as well as the timeout function may be used for further insurance. In yet a further embodiment, the attachment mechanism of the disposable feature or assembly may include a part that once removed from the device is either snapped off or is wait) to render it no longer attachable to a device. For example, the clip 125 in FIG. 2a may be adapted to snap off when the sleeve 120 is removed.

According to another embodiment, the sleeve portion, such as the sleeve 120, may be a limited reusable and disposable assembly or feature in a healthcare setting, such as a dentistry office or similar. For example, the disposable feature or assembly may also be autoclavable, even for a limited number of time.

In general, the sleeve 120 may protrude from the applicator end 102a of the housing 102 for a distance substantially coextensive with the end of the energy application tool 110 during measurement and may extend at least as far as the extended or propelled state of the energy application tool 110 as discussed above. Thus, the length of the sleeve portion 120 may be somewhat dependent on the length of protrusion of the extended energy application tool 110.

In some embodiments, as illustrated in FIG. 1f, the sleeve portion may be attached to or at the end of the housing 102 and being substantially perpendicular to it when the energy application tool 110, for example, a tapping rod, moves from being substantially parallel to making an acute angle with the longitudinal axis of the housing 102 at a pivot 110a when in operation. The sleeve portion may be substantially cylindrical in shape. In a further embodiment, the sleeve may be an extension of the housing and being of substantially a half cylindrical shape to allow the energy application tool, for example, the tapping rod to freely move when the tapping rod moves from being substantially parallel to making an acute angle with the longitudinal axis of the housing in operation. Using this system, measurements may be undertaken at locations which are relatively inaccessible such as, for example, in the molar area of a patient's teeth.

The sleeve 120 may generally include an object contact portion 123 which may be utilized to rest or press against the surface of an object, such as to stabilize and/or aid in repeatable positioning of the handpiece 100 against the object during a measurement. The sleeve portion may be substantially cylindrical and/or conical in shape with a hollow interior, as shown with the sleeve hollow portion 128 with a base portion 127 having an opening 126 where the energy application tool 110 may enter. The object contact portion 123 may generally form an aperture through which the energy application tool 110 may access the object. The size of the aperture may be varied, such as to provide a larger platform to rest against the object, as shown with the smaller aperture formed in the object contact portion 123 in FIG. 2f, or to provide a larger aperture, which may accommodate more varied object surfaces, as shown with the varied surfaces in FIGS. 3 and 3a.

In some embodiments, the aperture of the object contact portion 123 may further include a feature, for example, a contact feature, for contacting the object at an outer surface and the energy application tool 110 on an inner surface such that it may prevent direct contact between the energy application tool 110 and the object. This may be desirable to aid in preventing any contaminants or other sanitization concerns from moving between the object and the energy application tool 110 by providing a barrier. This may, for example, enable repeated use of the energy application tool 110 without cleaning/sterilizing/sanitizing it between, for example, different patients. The feature, such as the contact feature 121 as illustrated in FIGS. 1-1b and 2, 2b and 2c. In general, the contact feature 121 may be flexible, deformable and/or otherwise adapted to transmit the forces to and from the energy application tool 110 and the object during a measurement with minimal interference, attenuation or other undesired effects.

Figure 2B:
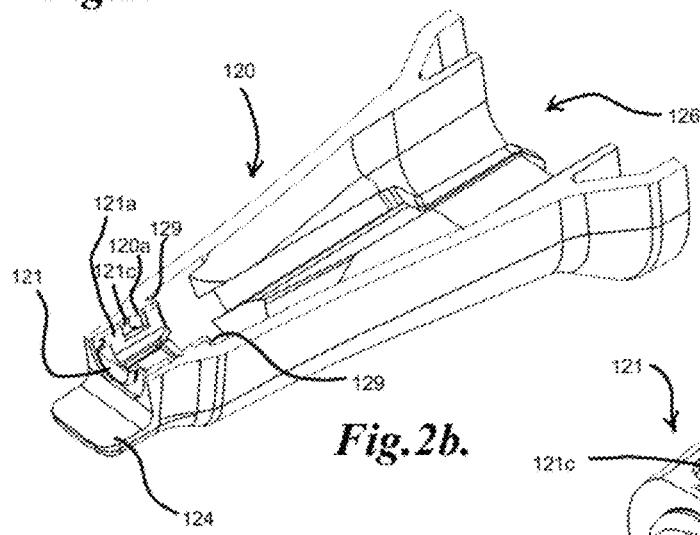
FIG. 2b illustrates a perspective cross-sectional view along a long axis of a sleeve portion with a contact feature.
Figure 2D:
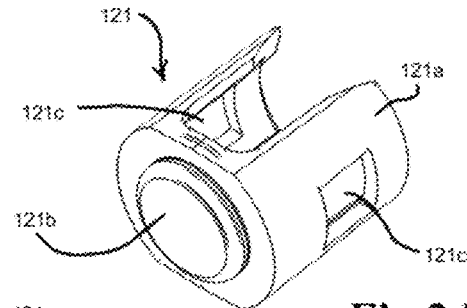
FIGS. 2d and 2e illustrate contact portions of a sleeve portion with movable or deformable portions.
Figure 2C:
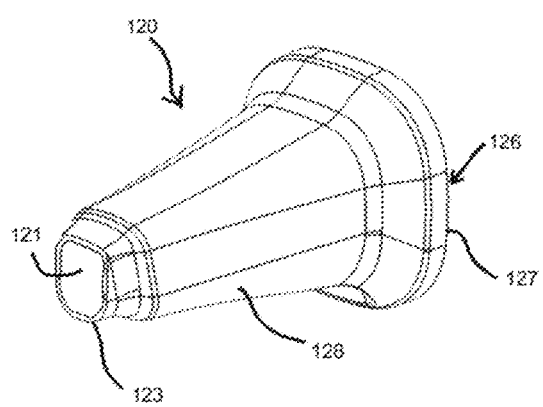
FIG. 2c illustrates a sleeve portion without a tab.
Figure 2E:
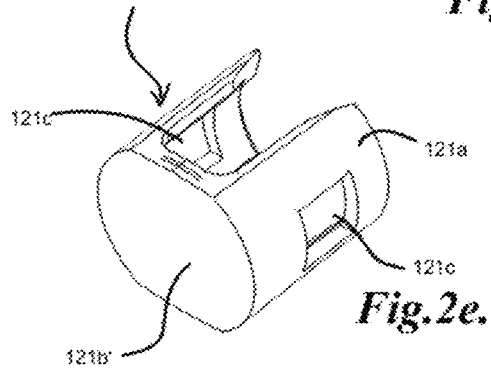
Figure 2F:
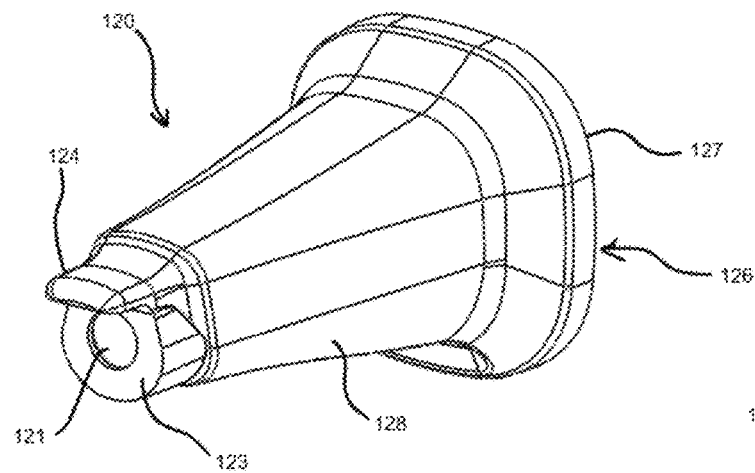
FIG. 2f illustrates a sleeve portion with a tab and enlarged contact surface.
Figure 2G:
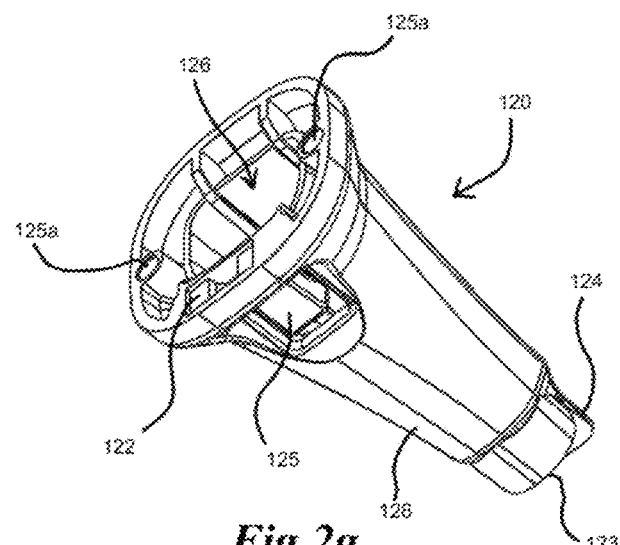
FIG. 2g illustrates a sleeve portion with a security feature, lighting interfaces and an attachment feature.
Figure 2H:
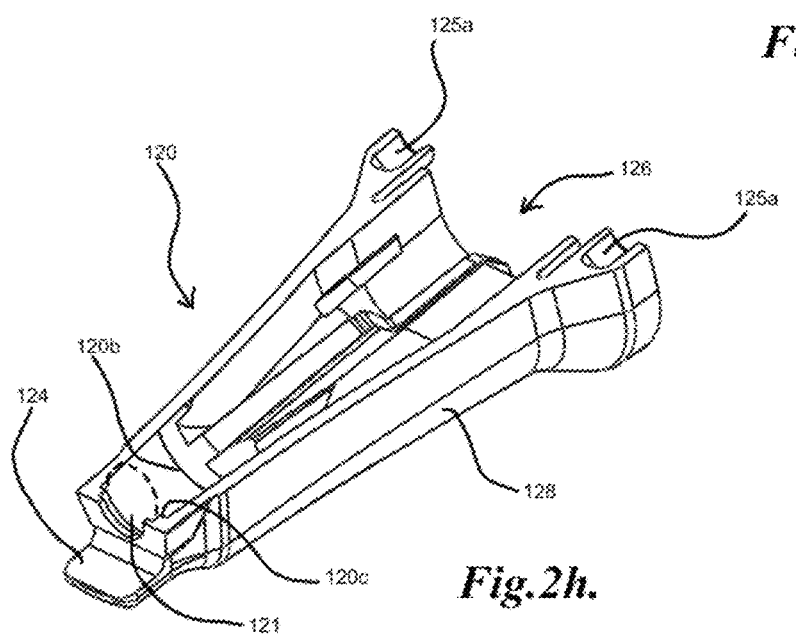
FIG. 2h illustrates a perspective cross-sectional view along a long axis of a sleeve portion with a contact feature and lighting interfaces.

In some exemplary embodiments, the contact feature 121 may be a separate component from the rest of the sleeve 120, as illustrated with the contact feature 121 in FIGS. 2b, 2d and 2e. A separate contact feature 121 may be desirable, for example, such that it may move at least semi-independently from the rest of the sleeve 120, as discussed further below. The separate contact feature 121 may be slidably and/or otherwise translatably disposed in the sleeve 120, as illustrated in the cross-sectional view of FIG. 2b, with the contact tubular portion 121a may rest in the sleeve 120, such as with a semi-frictional fit such that it is partially retained but may still move. The contact tubular portion 121a may also include features which may interact with corresponding features of the sleeve 120, such as to provide a limited range of motion, as illustrated with slots 121c and stop tabs 120a. In other embodiments, the contact feature 121 may be constrained by stops, ridges, bumps or other obstacles to prevent movement beyond a desired range along the longitudinal axis of the sleeve 120, such as illustrated with movement stops 120b, 120c in FIG. 2h.

In some embodiments, the contact feature 121 may include a thin membrane portion which may be of a thickness, deformability and/or shape such that it produces minimal effects on the transmission of forces through it. FIG. 2d illustrates an embodiment of a contact feature with a movable contact portion 121a which may include a thin membrane or other layer, as shown with separate contact portion 121b, which may move and/or deform freely, such as a thin plastic film or metal foil. In some other embodiments, such as in FIG. 2e, the contact feature 121 may be formed with an integral portion which may deform, flex and/or otherwise transmit the forces of the energy application tool 110, such as with a flexible plastic forming the contact feature 121 with a deforming contact portion 121b'. The movable contact portion 121a may also be formed to conform to the shape of the energy application tool 110, or vice versa, for optimal transfer of force/energy. In some exemplary embodiments, the movable contact portion 121a may be constructed from metallic foil, for example, stainless steel foil or sheet, and may, for example, be stamped and/or molded, for example, to conform to the end of energy application tool 110, such as with a domed shape. Some metallic foil or sheet, such as stainless steel and similar materials may be desirable, for example, due to its high strength characteristics such as rigidity or stiffness, ease of molding/forming, low dampening of transmitted energy or force through it, desirable properties for use in medical or dental applications and/or its commonality or low cost. For example, thin stainless steel foil or sheet, such as about 0.1 mm in thickness, may be utilized.

In other embodiments, the closed end of the contact feature 121 may be integral to the contact feature 121. For example, the contact feature 121 may be formed from a material which may be shaped into a tubular or ring structure with a closed end of a desired thickness, such as by stamping a metal (e.g. stainless steel, aluminum, copper, or other appropriate metal). For example, the contact feature 121 may take the form resembling a thimble or cup, with the closed end being of a thickness to provide deformable or movable characteristics.

For example, polymeric materials suitable for the, for example, membrane of contact feature may include any polymers having one or more of the following properties, including low coefficients of friction, high damping capacity, resorbable, biodegradable, water degradable, transparent, translucent and non-conductive.

For metallic material suitable for the, for example, foil or sheet, such as stainless steel and similar metallic material may be austenitic, work hardened, electro-polished, annealed prior to being formed into the desired shape, or superplastically formed into the desired shape.

In some embodiments, the contact feature 121 may be utilized to aid in producing consistent contact of the energy application tool 110 with the surface of an object, such as with surfaces with irregular or inconsistent surface features. For example, FIGS. 3 and 3a illustrate the use of the handpiece 100 with an object 90, where the object 90 has non-flat surface features, such as the object 90 with a convex contact surface 95 in FIG. 3 and another object 90 with a concave contact surface 96 in FIG. 3a. The object contact surface 123, which rests on the contact surface 94 of the object 90, may sit about an irregular or inconsistent surface feature which may provide a contact point for the energy application tool 110 either ahead or behind the plane of the object contact portion 123, as illustrated with the convex contact surface 95 protruding behind the plane in FIG. 3 and the concave contact surface 96 remaining ahead of the plane in FIG. 3a. With the contact feature 121 being movable with respect to the object contact surface 123, it may move and/or remain in an unextended or retracted position C, as shown in FIG. 3, to provide contact with the convex contact surface 95. Further, as shown in FIG. 3a, the movable contact feature 121 may move to an extended position D to provide contact with the concave contact surface 96. During a measurement, the energy application tool 110 may make an initial impact which may push the contact feature 121 to the proper position depending on the shape of the contact surface 94, and may remain substantially in that position or adjust to a different position in subsequent impacts or positionings of the handpiece 100. In general, the contact or impact of the energy application tool 110 may be controlled such that it does not cause deformation or damage to the object 90, but rather applies energy through properly accommodated contact as described.

In some exemplary embodiments, the sleeve 120 may include a feature for additional stability, such as providing stability substantially perpendicular or orthogonal to the direction A of the energy application tool 110. FIGS. 1a, 1b and 2-2b illustrate sleeve portions with a tab 124 protruding from the sleeve 120 near the object contact portion 123, such that when the object contact portion 123 is in contact with a surface of the object undergoing the measurement, the tab 124 may be resting on a portion of the top of the object, as shown with tab 124 resting on perpendicular surface 92 and object contact portion 123 resting on contact surface 94 of an object 90 in FIGS. 3 and 3a. The tab 124 and the object contact portion 123 may thus both assist in the repeatable positioning of the handpiece 100 with respect to the object 90 and the object contact portion 123 may be placed substantially at the same distance from the top of the object at perpendicular surface 92 during subsequent measurements for better reproducibility. As noted above, the object 90 may include an anatomical structure or a physical or industrial structure, though an anatomical structure is shown with a human tooth in FIGS. 3 and 3a.

In any of the embodiments, the corners of the tab 124 may be smooth or rounded or substantially smooth or rounded to avoid any catching on the object 90 they may be resting on. In other embodiments, the tab 124 may be smooth, though the corners may not necessarily be rounded.

In general, it may be desirable for the sleeve 120 or portions thereof to have sufficient rigidity such that it may consistently attach to the handpiece 100 and may not collapse during use. If multiple uses are contemplated, the sleeve 120 may generally be constructed to withstand multiple sterilization procedures, such as by autoclave, if desired, unless a disposable covering is used, as discussed below. In other embodiments, the sleeve 120 may be disposable, and if no sleeve is present, along with disposable coverings, if used, and thus may be constructed of any material that may be formed into a sleeve 120. Examples of appropriate materials may include, but are not limited to, for example, a polymer that may be molded, thermoformed or cast. Suitable polymers include polyethylene; polypropylene; polybutylene; polystyrene; polyester; polytetrafluoroethylene (PTFE); acrylic polymers; polyvinylchloride; Acetal polymers such as polyoxymethylene or Delrin (available from DuPont Company); natural or synthetic rubber; polyamide, or other high temperature polymers such as polyetherimide like ULTEM®, a polymeric alloy such as Xenoy® resin, which is a composite of polycarbonate and polybutyleneterephthalate, Lexan® plastic, which is a copolymer of polycarbonate and isophthalate terephthalate resorcinol resin (all available from GE Plastics); liquid crystal polymers, such as an aromatic polyester or an aromatic polyester amide containing, as a constituent, at least one compound selected from the group consisting of an aromatic hydroxycarboxylic acid (such as hydroxybenzoate (rigid monomer), hydroxynaphthoate (flexible monomer), an aromatic hydroxyamine and an aromatic diamine, (exemplified in U.S. Pat. Nos. 6,242,063, 6,274,242, 6,643,552 and 6,797,198, the contents of which are incorporated herein by reference), polyesterimide anhydrides with terminal anhydride group or lateral anhydrides (exemplified in U.S. Pat. No. 6,730,377, the content of which is incorporated herein by reference) or combinations thereof. Some of these materials are recyclable or be made to be recyclable. Compostable or biodegradable materials may also be used and may include any biodegradable or biocompostable polyesters such as a polylactic acid resin (comprising L-lactic acid and D-lactic acid) and polyglycolic acid (PGA), polyhydroxyvalerate/hydroxybutyrate resin (PHBV) (copolymer of 3-hydroxy butyric acid and 3-hydroxy pentanoic acid (3-hydroxy valeric acid) and polyhydroxyalkanoate (PHA) copolymers, and polyester/urethane resin. Some non-compostable or non-biodegradable materials may also be made compostable or biodegradable by the addition of certain additives, for example, any oxo-biodegradable additive such as D2W™ supplied by (Symphony Environmental, Borehamwood, United Kingdom) and TDPA® manufactured by EPI Environmental Products Inc. Vancouver, British Columbia, Canada.

In addition, any polymeric composite such as engineering prepregs or composites, which are polymers filled with pigments, carbon particles, silica, glass fibers, or mixtures thereof may also be used. For example, a blend of polycarbonate and ABS (Acrylonitrile Butadiene Styrene) may be used for the sleeve 120. For further example, carbon-fiber and/or glass-fiber reinforced plastic may also be used.

Synthetic rubbers may be, for example, elastomeric materials and may include, but not limited to, various copolymers or block copolymers (Kratons®) available from Kraton; Polymers such as styrene-butadiene rubber or styrene isoprene rubber, EPDM (ethylene propylene diene monomer) rubber, nitrile (acrylonitrile butadiene) rubber, and the like.

In some embodiments, the sleeve 120 may also be made of metallic and/or ceramic material(s) which may further be coated and/or treated with a suitable material, such as a polymer or composite as above. For example, a metallic and/or ceramic material may be utilized that may be substantially vibration dampening/absorbing/reflecting. A visco-elastic and/or other coating may also be employed such that vibrations and/or other mechanical energy may not translate into metallic and/or ceramic components of the sleeve 120.

In one embodiment, titanium and titanium alloys such as nickel-titanium, may be used for the sleeve 120, or components/portions thereof.

In a further aspect of the invention, the system may include features that aid in reliable and repeatable measurements from an object, such as by detecting the contact pressure of the for example, handpiece 100 against the object. As the contact by the sleeve portion aids to stabilize the handpiece on the object, during measurement, the force exerted by the energy application tool on an object and any measured characteristics may be affected by the force the operator exerts on the handpiece to hold it in place against the object. The proper amount of contact force on the object may be important and may need to be monitored, since, for example, either insufficient or excessive force exerted by an operator may complicate the measurements, and may even produce less accurate results. A sensor may be disposed inside the handpiece to measure such contact force, which may generally be not physically or mechanically coupled to the energy application tool 110, such that it may be aid in monitoring proper contact force applied by the operator for better reproducibility, even by different operators. In general, it may be desirable to isolate the energy application tool 110 from other parts of the system, such as the portions of the handpiece 100 which contact the object (besides the energy application tool 110 itself), such that they do not interfere with the application of energy or measurements taken or the interference is minimized.

In exemplary embodiments, a sensor may be disposed in a manner to measure the force exerted by the operator on the object via contact with the handpiece 100. For example, the sensor may thus be positioned, for example, between the object and the handpiece. The sensor may also be placed to receive transduced or transmitted force from the portion of the handpiece in contact with the object. The sensor may further be positioned between the handpiece and the operator in a manner that allows it capture the force applied. In some embodiments, an internal force sensor may be utilized which may rely on transduction or transmission of the normal force from contact with the object through portions of the handpiece 100. FIGS. 1, 1*d* and 1*e* illustrate an arrangement where the contact of a portion of the handpiece 100, such as the sleeve portion 120, may push (e.g. through contact at contact points 129 shown in FIGS. 2*b* and 4) on a force transfer member 130, such as a force transfer sleeve or sleeve-like component, which may then exert a force by pushing in direction B on a force sensor 143. In the exploded views of FIGS. 1*d* and 1*e*, the force sensor 143, for example, is sandwiched between a relative fixed component, as illustrated with the drive mechanism interface member 141, which itself is rigidly mounted to the drive mechanism 140 as discussed further below, and components that transfer force to the force sensor 143, as shown with the stacking of sleeve 120 (if present), transfer sleeve 112 and the sleeve mount 112*a*/force transfer member 130, which may pass through the apertures of the portions of the housing, as shown with forward end cap 105 and/or the sleeve mount PCB 108 and its retainer 107. The force sensor 143 may be, for example, held in a relative fixed position by mounting onto a rigid portion of the handpiece 100, such as the drive mechanism interface member 141, which may, for example, be coupled to drive mechanism 140 and/or to the housing 102 of the handpiece 100 such that it is in a relative fixed position with regard to the operator. The force sensor 143 may then detect the load originating from the contact with object 90 as biased against the relative fixed portion, such as the drive mechanism interface member 141. It may generally be understood that intervening components or portions between the object contact and the force sensor 143 may be present or not present so long as a full transduction/transmission path for the force remains for operation.

In some embodiments, as illustrated in FIGS. 1*c* and 1*e*, a force transducing or transmitting member may be utilized without the sleeve 120, as shown with force transfer member 130 and the transfer sleeve 112 in FIG. 1*e*, which may be used to contact the object.

Figure 4:
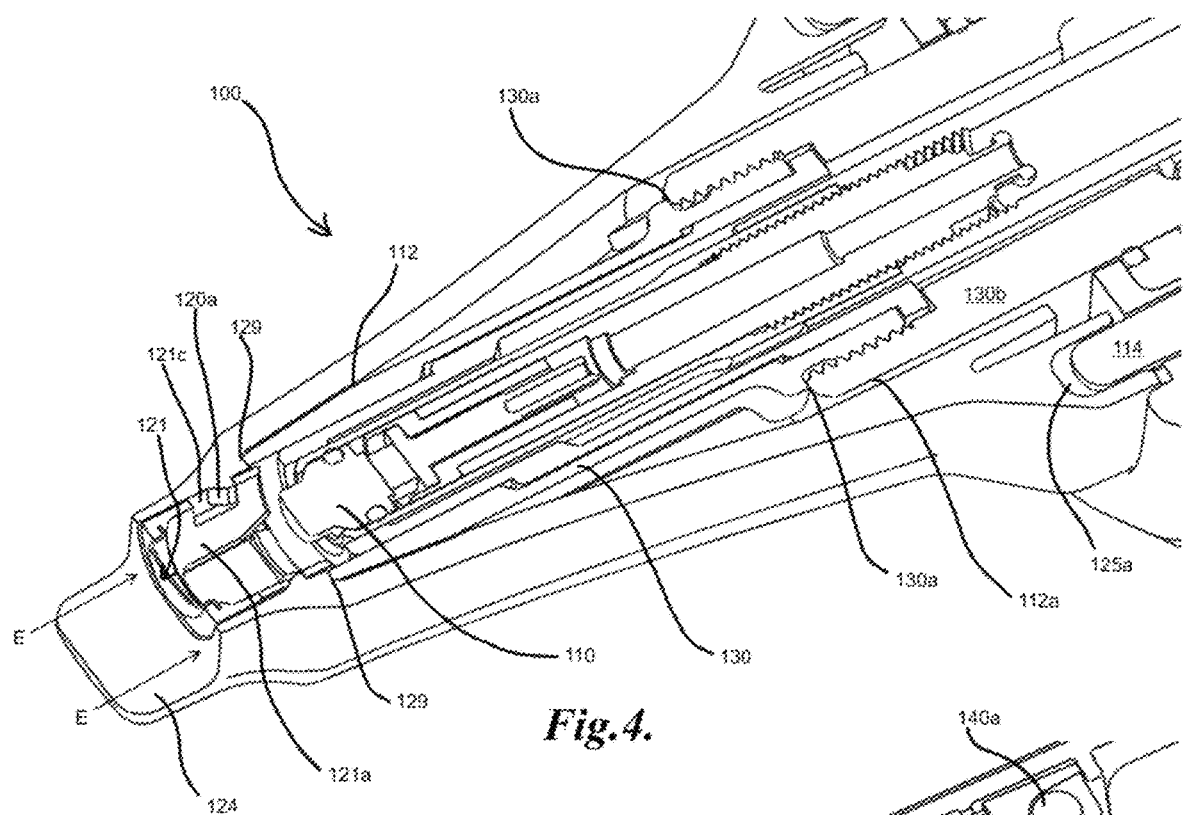
FIGS. 4, 4a and 4b illustrate transfer of contact force from an object to a force sensor.
Figure 4A:
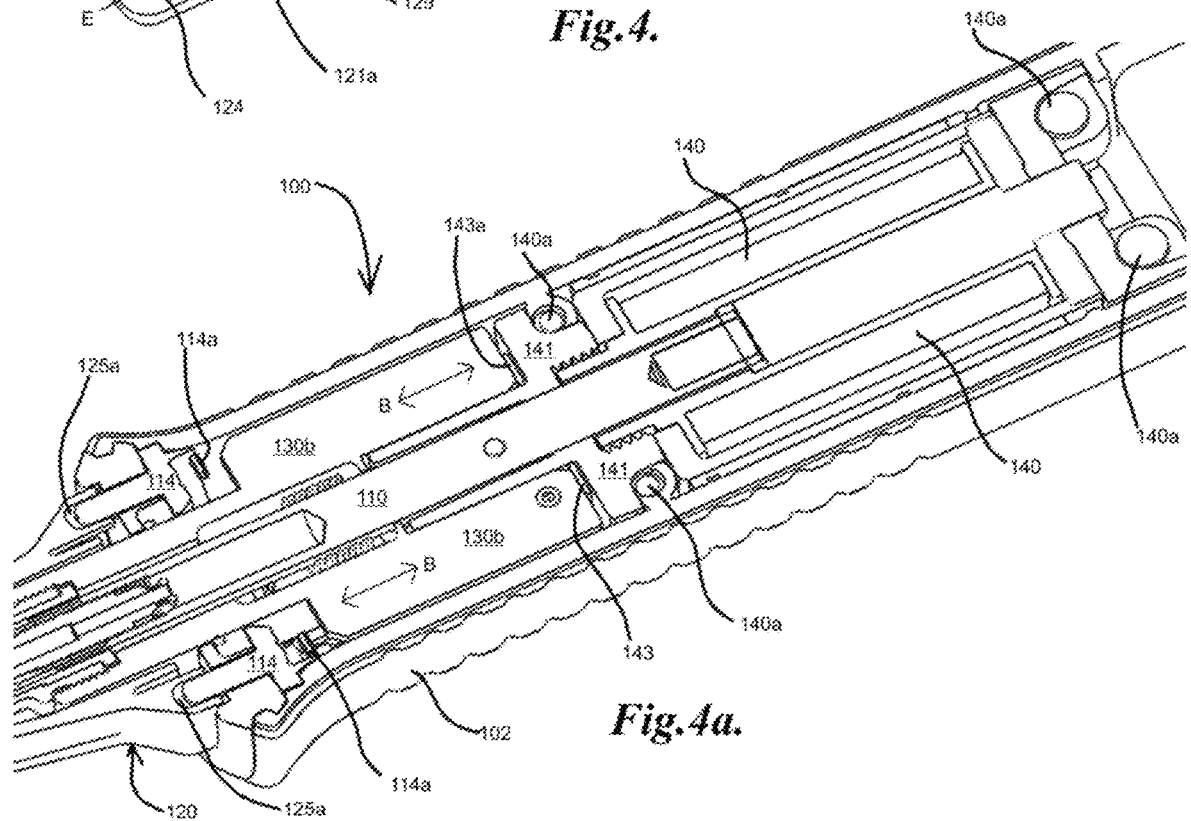
Figure 4B:
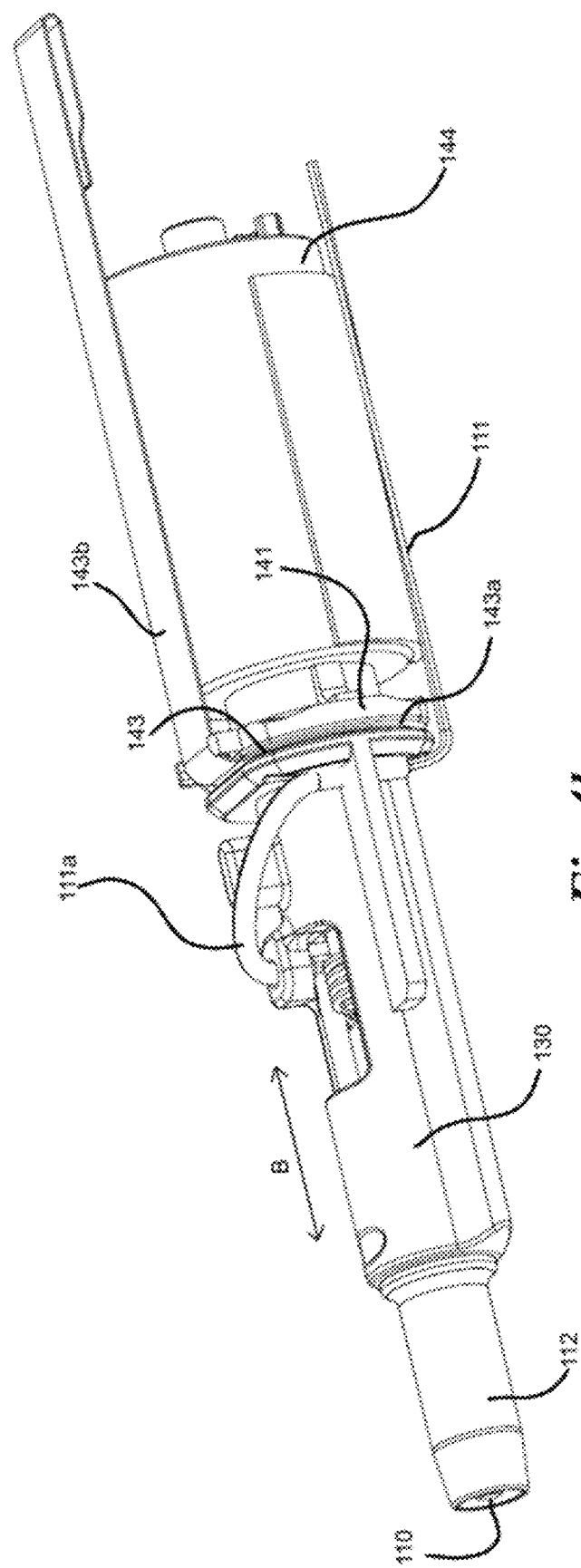

In embodiments of the system using a sleeve portion, a sleeve portion 120 may be mounted onto the force transfer member 130, such as onto sleeve mount 112*a* which may be coupled to or form a portion of force transfer member 130 and may extend out of the housing 102 via aperture 102*a*. The force from contact with the object may then be transferred, such as illustrated in FIGS. 4, 4*a* and 4*b*. As illustrated the normal force E from holding the sleeve portion 120 against the object may cause the sleeve 120 to push against the transfer sleeve 112, which may be a portion of or couple to the force transfer member 130, which may then exert the force in direction B on the force sensor 143, which may be biased against a rigid and/or relative fixed portion of the handpiece 100, such as the drive mechanism interface member 141, which may be mounted to the drive mechanism 140, which itself may be mounted to the housing 102, such as via drive mountings 140*a*.

In some embodiments, portions of the handpiece 100 may be movable relative to the rigid and/or relative fixed portion(s). This may be desirable to aid in transferring of force from the contact with the object to the force sensor and for providing a physically perceivable feedback to the operator of the exertion of contact force.

In some embodiments, multiple components may be utilized to form the force transfer member 130, such as for ease of manufacturing, assembly, replicability of parts, etc. For example, as illustrated, the force transfer member 130 may include separate parts transfer sleeve 112, sleeve mount 112*a* and force transfer base portion 130*b*, which may attach or at least contact to provide force transfer, such as at transfer member contacts 130*a*.

As illustrated in FIGS. 4 and 4*a*, the force transfer member 130 and its mechanically coupled portions, such as the sleeve portion 120, transfer sleeve 112, sleeve mount 112*a* and force transfer base portion 130*b*, may be movable, such as in direction B, relative to the relative fixed portions, such as the force sensor 143, drive mechanism interface member 141, drive mechanism 140 and housing 102. A biasing member, such as the force sensor bias 143*a*, may further be provided between the force transfer member 130 and the force sensor 143, such as to, for example, distribute the force on the force sensor 143 evenly and/or to serve as a return bias to return the force transfer member 130 to its original position along direction B when the contact with the object ceases, such as via a bias or leaf spring, or elastic cushion.

In general, the movement, such as the sliding distance, may be very small, for example, in the order of about 0.3 mm to about 1 mm, more for example about 0.5 mm.

In embodiments with an electrical contact between the sleeve portion 120 and the handpiece 100, such as the security feature 122 interacting with electronic contacts 113, movement between the sleeve 120 and the handpiece 100 may be compensated for, such as with spring pins and or placing electrical contacts such that contact is maintained through any motion of the sleeve 120 while mounted on the handpiece 100, such as by placement on parallel surfaces or on the movable portions, such as the sleeve mount 112*a*.

The sleeve portion 120 may also be mounted onto a force transfer member 130 that forms a permanent part on the front of the housing 102, and shields the energy application tool 110, for example, a tapping rod, from damage when no sleeve portion is present, for example, the sleeve portion forms part of a disposable assembly, as discussed above and/or below.

In some embodiments, as discussed above, the sleeve 120 and/or the energy application tool 110 may be disposed substantially perpendicular to the housing 102, as illustrated in FIG. 1*f*. The holding force against the object may then act in direction B, as illustrated, and as such the sleeve 120 may press in direction B against a force transfer member 130 onto a force sensor 143, which may be mounted and/or positioned against a relative fixed point, such as against the housing 102 as illustrated.

The energy application tool 110, for example, a tapping rod, may be enabled or triggered when the object contacting portion of the sleeve portion, such as the contact portion 121 of the sleeve 120, is pushed against an object undergoing measurement, for example, a tooth and a force within a certain range may be detected. When the correct force is detected, the handpiece 100 is turned on or enabled to start the measurement.

For example, with dental procedures on human teeth, an appropriate contact force may be about 3 N to about 10 N for example, more for example about 5 N to about 8 N of force. In general, the force sensor 143 may read the actual contact force or may read a transferred, transduced or transmitted force which differs from the actual contact force, which may be interpreted or correlated to the actual contact force by the handpiece 100, such as with electronics assembly 144. The measurement of the contact force may further be corrected, such as due to orientation of the handpiece 100 in the gravitational field, with input from an accelerometer or other appropriate device to detect orientation, as illustrated in FIG. 1 with orientation sensor 145.

The sensor, for example the force sensor 143, may be in physical proximity and/or contact and/or coupled with at least a portion of the handpiece 100 other than the energy application tool 110, for example, it may be in physical proximity and/or contact and/or coupled with the sleeve portion 120, if the open end of the sleeve portion 120 may include an object contacting portion 123, as noted above. In one embodiment of the invention, the sensor may include at least one strain gauge for sensing. The strain gauges may be attached or mounted to a cantilever between the device housing and the sleeve portion so that when the object contacting portion of the sleeve portion is pressed on the object it also deforms the cantilever which is measured by the strain gauge, thus providing a force measurement. In some embodiments, multiple strain gauges mounted to a single or to separate cantilevers may be utilized. The cantilever(s) may also, for example, be present on a separate component from the rest of the housing or sleeve portion, such as, for example, on a mounting device. According to one aspect, the force sensing may be done by a linear position sensor, which would know, for example, that if the force transfer sleeve like portion is at position X, a force of Y has to be applied to it (against the reaction force of the spring) to move it to that position. According to another aspect, the force sensing may be performed by an optical sensor, for optically sensing the position of the moving part, when it is pushed against a spring. In yet another embodiment of the invention, the relative position of the object contacting portion of the sleeve portion on the object may be determined by having one or more strain gauges which may be attached at one end to a moving part, for example, a force sensor sleeve like component, and the other end to a static element, for example, the housing. In a further embodiment of the invention, the device may include piezoelectric elements for directly measuring the force. In yet a further embodiment of the invention, a hall effect sensor may be used to detect a change in the magnetic field when a magnet (attached to the moving element) is moving relative to the position of the sensor. In yet another embodiment of the invention, a capacitive linear encoder system, like that found in digital calipers may be used to measure the force.

The sensing pad may include a layer structure, which may be generally referred to as a "Shunt Mode" FSR (force sensing resistor) that may change resistance depending on the force applied to the pad, to provide a force measurement. FSRs typically consist of a conductive polymer, which changes resistance in a predictable manner following application of force to its surface. The sensing film of the FSR typically includes both electrically conducting and non-conducting particles suspended in a matrix. Applying a force to the surface of the FSR causes particles to touch the conducting electrodes, changing the resistance of the FSR. FSRs may be desirable for their low size, such as with a thickness typically less than 0.5 mm, low cost and good shock resistance.

Figure 6:
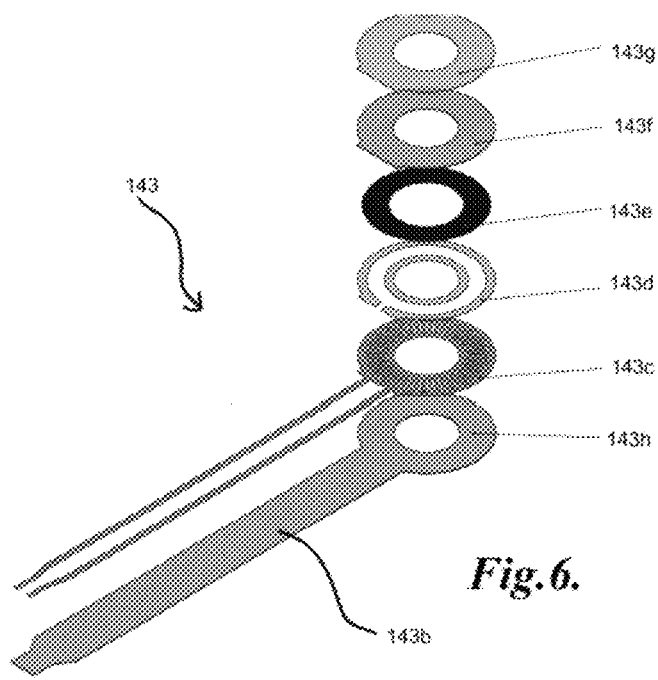
FIG. 6 illustrates a layered force sensor.

FIG. 6 illustrates an example of a layered force sensor 143 which may include a base layer 143*h* on which is printed or otherwise deposited a conductive trace 143*c* with two conductive pathways which are joined by an FSR layer 143*e* on an FSR substrate 143*f* to produce a conductive pathway modulated by the resistance of the FSR layer 143*e*. Pressure applied to the FSR layer 143*e*, such as in the direction B from the force transfer member 130, may alter its resistance, such as by decreasing it with applied pressure. Adhesive layers, such as adhesive layer 143*d* and mounting adhesive 143*g*, may also be included to join layers together and/or to provide adhesion to a substrate, such as to the drive mechanism interface member 141. The force sensor 143 may generally include a connector, such as flexible connector 143*b* shown in FIGS. 1*d* and 1*e*, to connect to an interface on electronics assembly 144, such as by carrying connections to the conductive pathways in the conductive trace 143*c*.

Piezoelectric sensors may also be utilized that convert pressure exerted on the force sensor 143 into a change in electrical characteristics, such as a voltage across the piezoelectric element.

A strain gauge or other similar element may also be included on a leaf spring or other biasing member, such as the force sensor bias 143*a*.

In some exemplary embodiments, the force sensor may be in electronic communication with the energy application tool 110 and may act as an on/off switch or activation switch for the handpiece 100. For example, when a proper force is exerted on the object by the object contacting portion of the sleeve, it may trigger the activation mechanism of the instrument to activate the movement of the energy application tool 110 to start a measurement. Thus, no external switches or push buttons are needed to activate the on and off of the system, as noted above. The indication of the proper force may be indicated by visible or audible signals.

Figure 7:
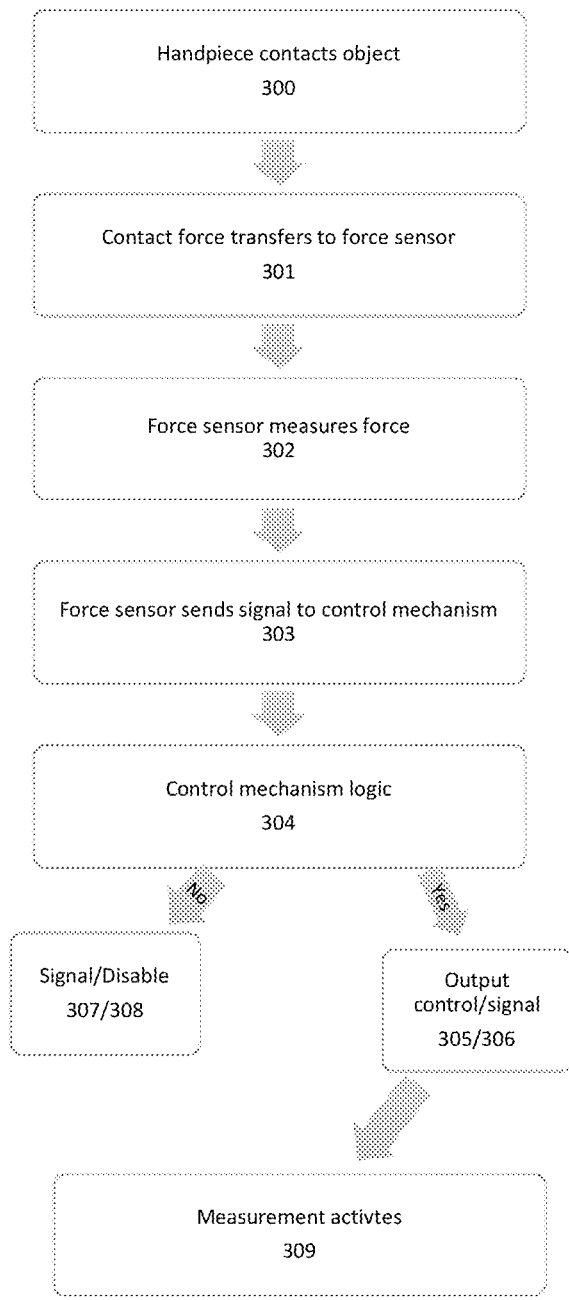
FIG. 7 shows a flowchart of operating a handpiece to place and take a measurement from an object.

In some embodiments, as illustrated with the flow chart in FIG. 7, the contact of the handpiece 100 with the object 90 (300), such as with the sleeve portion 120 may transfer contact force, such as the normal force E from the contact, to the force sensor 143 (301). The force sensor 143 may measure the contact force or a transferred force and produce a signal or change in characteristic, such as resistance, voltage, etc. (302). The signal or change in characteristic may then be relayed to the control mechanism, such as in the electronics assembly 144 (303). The control mechanism may then determine if the contact force is in an acceptable range, for example 5-8 N (304). If the force is in the range, the control mechanism may enable the energy application tool 110 to operate (305) and/or output a signal to the user that the contact force is acceptable (306). If the contact force is out of the acceptable range, the control mechanism may output a signal to the user to change the pressure (307) and/or disable or keep disabled the energy application tool 110 (308). If acceptable, the control mechanism may also initiate the energy application tool 110 automatically and perform a measurement (309). Afterwards, the control mechanism may be reset for a new measurement.

In some embodiments, the energy application tool 110 may be instantaneously turned on once a proper contact force is exerted by the contact portion 121 (or other portion of the sleeve 120 or handpiece 100, as appropriate) on the object, as indicated by visible or audible signals. FIG. 1*c* illustrates operator signals, as shown with light sources 114, which may provide signals to the operator about the contact force. In some embodiments, there may be a delay prior to activating the energy application tool 110 once a proper contact force is exerted on the object, as indicated by visible or audible signals, as above. In a further embodiment, once a certain push force on the object is detected and maintained for a period of time, for example, about 0.5 seconds, the instrument may be turned on to start measurement.

In some embodiments, the force measurement may be connected to a visual output, such as lights. Lights may be mounted at any convenient location on the instrument, for example, one or multiple LEDs may be mounted at the front of the instrument, as shown with light sources 114. For example, a multiple light system may be included. For example, two LEDs may be used, such as green for acceptable and red for unacceptable contact force.

In some embodiments, a light from the light sources 114 lights up the sleeve 120, which may be transparent or translucent, to indicate acceptable or unacceptable contact force.

The proper force exerted by the operator on the object acts as a switch of the system. When the system is not switched on, it may be desirable to know whether it has malfunction, not sufficient force or too much force is exerted. In some embodiments, if the user is pushing too hard on the object, the light may change first to amber, then to red, such as indicated via output from the light sources 114. If the push force is sufficient to change the light to red, percussion may either not be started, or be interrupted if it has already started. In addition, there may be an amber LED state which warns when the user is approaching too much push force. At that stage, the instrument may still operate when the LEDs are lit amber. In another example, no light may indicate too little force, a green light may indicate the right amount of force, while a red light may indicate too much force. In yet another example, a one light system may be included. For example, no light may give a signal of too little force and a red light may give a signal of too much force. In a further example, a flashing red light may indicate too much force and no light may indicate too little force. The LEDs may be mounted on the surface of the handpiece 100, or they may be internal to the housing 102 and light may be conveyed via light pipes or fiber optic channels, which may present at the surface of the housing 102, such as at the light sources 114 shown as light pipes in FIG. 1*d*. In some examples, the light pipes 114 may be integral or attached to a portion of the handpiece 100, such as being integral or attached to the retainer 107' in FIG. 1*g*, which may be substitute retainer 107 in FIG. 1*d*.

In some embodiments, the light pipes 114 may extend into the sleeve portion 120 such as to better carry light toward the object and/or to better illuminate the sleeve portion 120 for a user's perception. FIGS. 4 and 4*a* illustrate light pipes 114 extending from the handpiece 100 to carry light from the light sources 114*a* into the sleeve portion 120, as shown by extending into slots 125*a* in the sleeve portion 120. Light emanating from the light pipes 114 may then illuminate the sleeve portion 120, which may, for example, be adapted to diffuse the light toward the object and/or in a manner to be easily observable by the user, such as by inclusion of light diffusing material(s), additive(s) and/or by physical treatment, such as frosting and/or any other appropriate treatment. The light pipes 114 may also be utilized to provide additional alignment, connection and/or securement between the sleeve portion 120 and the handpiece 100, such as by fitting into the slots 125*a* of the sleeve portion 120. For example, the utilization of one or more light pipes 114 fitting into slots 125*a* may aid in providing resistance to rotation about the longitudinal axis by the fitting between the light pipes 114 and the slots 125*a* (e.g. by close or friction fitting).

In another embodiment, the force measurement may be connected to an audible output. In one example, the audible output may include a beeping sound to indicate too little force and a multiple beep to indicate too much force. In another example, the audible output may include a beeping sound to indicate too little force and a beeping sound with a flashing red light to indicate too much force, such as via the light sources 114 or as discussed above with internal light sources. In a further example, the force measurement may be connected to a voice alert system for alerting too much force or too little force. In yet a further example, the force measurement may be connected to a voice alert system to alert too little force and a voice alert and a flashing red light for alerting too much force.

The handpiece 100 may also include a reset button, such as shown with reset control 144*b* in FIG. 1*d*, such as to reset the handpiece 100 to re-attempt placement with a proper force after an initial incorrect placement. The reset button 144*b* may press onto an appropriate control on the electronics assembly 144 to place the handpiece 100 in a renewed state.

When the force sensor acts as an on/off switch, it may also act to monitor that a proper force is exerted on the object during measurement and/or a proper alignment of the handpiece 100 against the object during measurement is obtained. An inclinometer as shown with orientation sensor 145 in FIG. 1, may be present, for example, as part of an electronic control system, which may trigger an audible warning when the device is outside of the angular range of operation, for example, for a tapping rod, it may trigger the warning when it is plus/minus 30 degrees from horizontal. If the device is oriented such that the axis of operation is greater than 30 degrees from horizontal when a push force is sensed on the object contacting portion of the sleeve portion, it may result in a warning sound being emitted by a speaker located on the device, such as the PCB within the device. In such circumstances, the percussion action will not begin until the device is returned to an acceptable angle. In some instances, if the percussion action has started when the above mentioned departure from the range is detected, the device may not actually stop operation, but may simply be sounding an alarm, so that corrections may be made.

Common implementations of tilt sensors and inclinometers may include, but are not limited to, accelerometer, liquid capacitive, electrolytic, gas bubble in liquid, and pendulum-type systems. Traditional spirit levels and pendulum-based electronic leveling instruments are usually constrained by only single-axis and narrow tilt measurement range. However, most precision leveling, angle measurement, alignment and surface flatness profiling tasks essentially involve a two-dimensional surface plane angle rather than two independent orthogonal single-axis objects. Two-axis inclinometers are typically built with micro electromechanical systems (MEMs) tilt sensors provides simultaneous two-dimensional angle readings of a surface plane tangent to earth datum.

MEMS tilt sensors typically employ accelerometers for functionality. Conceptually, an accelerometer behaves as a damped mass on a spring, where the accelerometer experiences an acceleration and the mass is displaced to the point that the spring is able to accelerate the mass at the same rate as the casing. The displacement is then measured to give the acceleration. In commercial devices, piezoelectric, piezoresistive and/or capacitive components are commonly used to convert the mechanical motion into an electrical signal. Piezoelectric accelerometers rely on piezoceramics (e.g. lead zirconate titanate) or single crystals (e.g. quartz, tourmaline). They typically offer favorable characteristics in application, such as upper frequency range, low packaged weight and high temperature range. Piezoresistive accelerometers are typically preferred in high shock applications. Capacitive accelerometers typically use a silicon micromachined sensing element, where their performance is superior in the low frequency range and they can be operated in servo mode to achieve high stability and linearity. Modern accelerometers are often small MEMs comprising a cantilever beam with a proof mass. Damping results from the residual gas sealed in the device. Under the influence of external accelerations the proof mass deflects from its neutral position. This deflection is measured in an analog or digital manner.

The device and/or a portion of the housing may also have an antimicrobial coating coated thereon capable of eliminating, preventing, retarding or minimizing the growth of microbes, thus minimizing the use of high temperature autoclaving process or harsh chemicals and may increase the kind and number of materials useful as substrates for making such tools or instruments.

Further, the instrument may be useful in aiding in the selection of material, such as mechanically biocompatible material, or biomemetically compatible material used in the construction of and/or selection of a material for an anatomical structure, for example, an implant. For normal healthy teeth, the percussive energy generated by mastication is attenuated by the periodontal ligament at the healthy bone-natural tooth interface. However when an implant replaces natural tooth due to damage or disease, the ligament is generally lost and the implant may transmit the percussive forces directly into the bone. Several materials such as composites, gold, zirconia and so on, used to fabricate the implant abutment have been shown to be effective in numerous studies. While studies have demonstrated the survivability of implant restorations utilizing composite resin, gold or zirconia abutments after construction of the abutments, there has been no such research done to measure the dynamic response to load of said abutment materials. The instrument of the present invention may be used for such purposes and may be useful to predict the suitability or compatibility prior to implantation, or to choose suitable materials to protect natural teeth adjacent the implants. Thus, the choice of materials may minimize the disparity between the way the implants and natural teeth respond to impact.

Furthermore, the instrument may be useful in aiding in the selection of material, such as mechanically or chemically durable or compatible material, used in the construction of and/or selection of a material for, for example, a plane, an automobile, a ship, a bridge, a building, any industrial structures including, but limited to power generation facilities, arch structures, or other similar physical structures or damping material suitable to aid in the construction of such structures. The instrument of the present invention may be used to such purposes and may be useful to predict the suitability of a material prior to construction in addition to detection of cracks, fractures, microcracks, cement failures, bond failures or defect location, etc., after the construction.

In addition, the present invention is also useful in distinguishing between defects inherent in the material making up the structure or object, and cracks or fractures, etc., as discussed above due to trauma or wear or repeated loading. Defects inherent in the bone or material construction of an implant, or a physical structure, for example, may include lesions in the bone, similar defects in the implant construction or manufacturing of polymer, polymer composites or alloys, or metallic composites or alloys.

The stabilization of the instrument by the sleeve portion or contact feature, and/or tab or the tab and/or component may also minimize any jerky action that may confound the testing results, for example, any defects inherent in the bone structure or physical or industrial structure may be masked by jerky action of the tester. This type of defect detection is important because the location and extent of the defect may impact dramatically upon the stability of the implant or physical or industrial structures. Generally when lesions are detected, for example, in an implant, such as a crestal or apical defect, the stability of the implant may be affected if both crestal and apical defect are present. In the past, there is no other way of gathering this type of information other than costly radiation intensive processes. With the present invention, this type of information may be gathered, and may be done in an unobtrusive manner.

In general, the present invention further represents a new form of precision of risk assessment in dental health or structural integrity of physical structures and an opportunity to diagnose in a new manner. The present invention provides for the administering of kinetic energy to the specimen, loading and displacement rates that may be determined by the specimen, deceleration measured upon impact and analysis of dynamic mechanical response for more accurate prediction of cracks, fractures, microcracks, microfractures; loss of cement seal; cement failure; bond failure; microleakage; lesions; decay; structural integrity in general; structural stability in general or defect location.

Further, multiple indicators of structural integrity, such as LC (loss coefficient) and ERG (energy return graph) may be possible as well as percussion loads in a critical direction. The present system provides a convenient and easy way of providing buccal loading and other loading directions are possible such as the lingual direction for testing the structural properties mentioned above.

Buccal loading is important in that it is typically the more dangerous type of loading encountered by, for example, a tooth. In general, vertical loading induces relatively low stresses in teeth. However, working and/or nonworking motion produces side loading as a result of the lateral motion of the jaw and inclined geometries of the occlusal surfaces of teeth and restorations. This side loading may induce much higher stress concentrations at external and internal surfaces and below the margin. Thus, using the system of the present invention, such tests may be easily performed. In short, the system not only is adapted for detection of structural stability, integrity, cracks, etc., of a prosthetic dental implant structure, a dental structure, an orthopedic structure, or an orthopedic implant, but may also be adapted for use in the actual construction and replacement process through testing under stresses that may be encountered later after implantation.

Natural loading is typically pulsatile (as opposed to for example sinusoidal). Muscular, cardiovascular, running, jumping, clenching/bruxing, so on, all may produce loading, for example, pulsatile loading. Percussion loading is pulsatile and therefore physiological. Percussion loading may be used to measure visco-elastic properties and detect damage in a structure.

As mentioned above, the present invention provides the ease and speed of application and may be employed to detect and assess microleakage, gross recurrent decay, loose post/build-up, decay in post space, whether tooth is non-restorable, gross decay, near pulp exposure, enamel and dentinal cracks, internal alloy fracture, or even any bioengineering mismatch, any defect that create movement within the structure, and so on in a non-destructive manner. This is also true of industrial or physical structures noted above. Although the invention has been described with respect to specific aspects, embodiments and examples thereof, these are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein, the meaning of "in" includes "in" and "on" unless the context clearly dictates otherwise.

The invention claimed is:

1. A device for determining structural characteristics of an object, comprising:
   a housing having a hollow interior, an open front end and a longitudinal axis;
   an energy application tool mounted inside said housing for movement, said energy application tool having a resting configuration and an active configuration;
   a drive mechanism supported inside said housing, said drive mechanism being adapted for moving said energy application tool between said resting and active configurations; and
   a disposable feature adapted for enveloping a portion of said device, said disposable feature comprising:

a sleeve portion having a longitudinal axis and protruding from said open front end of said housing for a distance, said sleeve portion having a hollow interior with a front end and a rear end and an object contacting portion at the front end adapted for resting, contacting or pressing against at least a portion of said object with at least a portion of said object contacting portion; and a contact feature disposed inside the sleeve portion adapted for freely moving or sliding inside said sleeve portion along said longitudinal axis of said sleeve portion, said contact feature having a body with a length and a substantially closed front end for substantially closing off the open front of the sleeve portion to minimize direct contact between said energy application tool and said object during measurement.

2. The device of claim 1 wherein said closed front end of said contact feature comprises a movable contact portion or a deforming contact portion.

3. The device of claim 1, further comprising a tab extending from said sleeve portion substantially perpendicular to said object contacting surface of said sleeve portion.

4. The device of claim 1, further comprising a sensor adapted for sensing a contact force when said object contacting portion of said sleeve portion presses on said object.

5. The device of claim 4 further comprising a movable force transfer sleeve like component disposed towards the open front end of the housing for transferring said contact force between said sleeve portion and said object to said sensor.

6. The device of claim 1, wherein said front end of said contact feature comprises a thin membrane.

7. The device of claim 1, further comprising a chip for communicating with a transceiver in said device for authenticating that the disposable feature is new or unused.

8. A system for determining structural characteristics of an object, comprising:
a device having a housing with an open end and a longitudinal axis;
an energy application tool mounted inside said housing for applying energy to said object, said energy application tool having a resting and an active position;
a drive mechanism supported inside said housing and coupled to said energy application tool, said drive mechanism adapted for repeatedly moving said energy application tool from said resting to said active position;
a sleeve portion protruding from said open end of said housing for a distance, said sleeve portion having an object contacting portion at its free open end and is adapted for contacting at least a portion of said object with at least a portion of said object contacting portion of its open end;
an internal on/off switch for the device comprising:
a sensor positioned inside said housing for monitoring a contact force between said object contacting portion of said sleeve portion and said object when at least a portion of said object contacting portion of said sleeve portion contacts at least a portion of the object, said sensor not being directly physically coupled to said energy application tool; and
a movable force transfer sleeve like component disposed at the front of the housing for transferring said contact force from said sleeve portion to one end of said sensor, said transfer sleeve like component is adapted for translational movement;
wherein said sensor activates said drive mechanism when said exerted contact force is in a predetermined range.

9. The system of claim 8 further comprising a computer coupled to said device adapted for determining structural characteristics of said object.

10. The system of claim 9, further comprising a base station for pairing to said device prior to use.

11. The system of claim 10 wherein said device further comprises a wireless transceiver, and said base station is adapted for charging the device, and acts as a wireless transceiver for the computer in communicating with said wireless transceiver in the device.

12. The device of claim 9, further comprising at least one light source disposed in said housing and at least one light pipe extending from said housing into said sleeve portion to carry light from said at least one light source.

13. The device of claim 12, where said at least one light pipe is adapted to constrain movement of the sleeve portion relative to the housing.

14. The system of claim 8, wherein said predetermined range of the exerted contact force is between about 1 Newtons to about 40 Newtons.

15. The system of claim 8, wherein said translational movement of said transfer sleeve like component is triggered when at least a portion of said object contacting portion presses upon at least a portion of said object for a distance.

16. The system of claim 8, wherein a second end of said sensor is in contact with a static element of or inside said housing.

17. The system of claim 8, wherein said sensor comprises a sensing pad, at least one strain gauge, a linear force sensor, an optical sensor, a piezoelectric element, or a hall effect sensor.

18. A system for determining structural characteristics of an object, comprising:
a device having a housing with an open end and a longitudinal axis;
an energy application tool mounted inside said housing for applying energy to said object, said energy application tool having a resting and an active position;
a drive mechanism supported inside said housing and coupled to said energy application tool adapted for repeatedly moving said energy application tool from said resting to said active position;
a sleeve portion protruding from said open end of said housing for a distance, said sleeve portion having an object contacting portion at its free open end and is adapted for contacting at least a portion of said object with at least a portion of said object contacting portion of its free open end;
a force sensor coupled with at least a portion of said device but not physically coupled to said energy application tool is positioned inside said housing for monitoring a contact force between said object contacting portion of said sleeve portion and said object; and
an inclinometer positioned inside said housing for monitoring the inclination of the device in relationship to the horizontal orientation;
wherein said contact force activates said driving mechanism of the energy application tool to start a measurement when a proper force is exerted on said object by said object contacting portion of said sleeve and the device is not outside of the angular range of plus/minus approximately 45 degrees with respect to the horizontal orientation.

19. The system of claim 18 further comprising a movable force transfer sleeve like component disposed towards the open end of the housing for transferring said contact force between said sleeve portion and said object to said sensor.

20. The system of claim 18, wherein said sleeve portion protrudes from said open front end of said housing in a substantially parallel or substantially perpendicular direction to the longitudinal axis of said housing.

21. The system of claim 18, further comprising a contact feature disposed inside the sleeve portion adapted for freely moving or sliding inside said sleeve portion along said longitudinal axis of said sleeve portion, said contact feature having a body with a length and a substantially closed front end for substantially closing off the open front of the sleeve portion to minimize direct contact between said energy application tool and said object during measurement.

\* \* \* \* \*